United States Patent [19]
Cordi et al.

[11] Patent Number: 6,127,396
[45] Date of Patent: Oct. 3, 2000

[54] IMIDAZOLINE COMPOUNDS

[75] Inventors: Alex Cordi, Suresnes; Jean-Michel Lacoste, Sevres; Mark Millan; Adrian Newman-Tancredi, both of Le Pecq; Alain Gobert, Rueil-Malmaison, all of France

[73] Assignee: Adir et Compagnie, Courbevoie, France

[21] Appl. No.: 09/466,716

[22] Filed: Dec. 17, 1999

[30] Foreign Application Priority Data

Dec. 18, 1998 [FR] France ..................... 98 15999

[51] Int. Cl.$^7$ .................... A61K 31/415; C07D 233/02; C07D 233/08

[52] U.S. Cl. .................. 514/396; 514/397; 548/311.4; 548/347.1

[58] Field of Search .................... 514/397, 396; 548/311.4, 347.1

[56] References Cited

FOREIGN PATENT DOCUMENTS 01242571  9/1989  Japan .

*Primary Examiner*—Zinna Northington Davis
*Assistant Examiner*—Binta Robinson
*Attorney, Agent, or Firm*—The Firm of Gordon W. Hueschen

[57] ABSTRACT

The invention relates to a compound of formula (I):

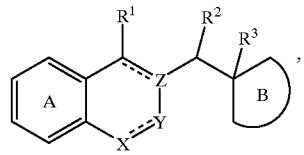

(I)

wherein:
  A represents an optionally substituted benzene ring,
  B represents an imidazoline ring of formula (Ia) or (Ib):

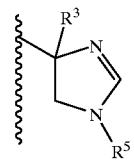

(Ia)

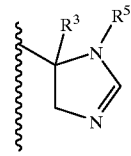

(Ib)

X represents $CR^6$, $CR^6R^7$, $NR^8$, SO or $SO_2$, or oxygen, nitrogen or sulphur,
Y represents a single bond or CH or $CH_2$,
Z represents a carbon atom or $CR^4$,
$R^1$, $R^2$, $R^3$, which may be the same or different, each represent hydrogen or alkyl, it being possible for ($R^1$ and $R^4$) or ($R^2$ and $R^4$) to form cyclopropane,
$R^5$ represents hydrogen, alkyl or benzyl.

23 Claims, No Drawings

IMIDAZOLINE COMPOUNDS

FIELD OF THE INVENTION

The present invention relates to new imidazoline compounds and also to their use as α2-adrenergic antagonists and monoamine (serotonin and/or noradrenaline) reuptake blockers.

DESCRIPTION OF THE PRIOR ART AND BACKGROUND OF THE INVENTION

The adrenergic nervous system plays an important role at a number of levels, for example at arterial, venous, cardiac and renal level, and at the level of the central and peripheral autonomic nervous systems. Compounds capable of interacting with adrenergic receptors can thus induce a large number of physiological responses, such as vasoconstriction, vasodilation, an increase or decrease in cardiac rhythm, variation in the strength of contraction of the cardiac muscle and variation in metabolic activities. Various adrenergic compounds have been used in the past for modifying these or other physiological responses.

In addition to the fact that the compounds described in the present invention are new, they have an α2-adrenergic antagonist and monoamine reuptake-blocking profile, rendering them of use in the treatment of depression (Drug News & Perspective, 4 (4), 1991). The main problem posed by antidepressants is that they take a long time to become effective, associated with their particular manner of action. Studies have demonstrated that the association of an α2-adrenergic antagonist with an inhibitor of monoamine reuptake made it possible to reduce that length of time (Commun. Psychopharmacol, 4, pp. 95–100, 1980). The combination of those two effects in a single compound could give rise to a new generation of much more effective antidepressants. Among those compounds, napamezole (U.S. Pat. No. 5,017,584) is described as having both an α2-adrenergic antagonist activity and a monoamine reuptake-blocking activity.

The compounds of the present invention, which have new structures, have a selective α2-adrenergic antagonist profile and an ability to inhibit monoamine reuptake which is surprisingly superior to napamezole.

DETAILED DESCRIPTION OF THE INVENTION

More specifically, the present invention relates to compounds of formula (I):

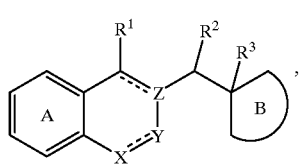

(I)

wherein:

A represents a benzene ring unsubstituted or substituted by from 1 to 4 identical or different groups selected from linear or branched ($C_1$–$C_6$)alkyl, linear or branched ($C_1$–$C_6$)alkoxy, hydroxy, polyhalo-($C_1$–$C_6$)alkyl in which the alkyl moiety is linear or branched, cyano, nitro, amino, alkylamino, dialkylamino, thioalkyl, sulphonylalkyl, sulphinylalkyl, carboxy, alkoxycarbonyl, alkylcarbonyloxy, formyl, carbamoyl, carboxamide, phenyl, benzyl, and halogen atoms, B represents an imidazoline ring as represented in formula (Ia) or (Ib):

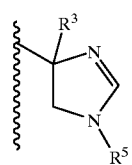

(Ia)

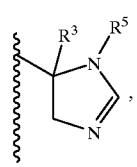

(Ib)

X represents
a $CR^6$ or $CR^6R^7$ group (wherein $R^6$ and $R^7$, which may be the same or different, each represent a hydrogen atom or a linear or branched ($C_1$–$C_6$)alkyl group),
a nitrogen atom or an $NR^8$ group (wherein $R^8$ represents a hydrogen atom or a linear or branched ($C_1$–$C_6$)alkyl group or a benzyl group),
an oxygen atom,
a sulphur atom or an SO or $SO_2$ group,
Y represents a CH or $CH_2$ group or a single bond (and, in that case, the ring containing X, Y and Z is represented by the formula (Ic):

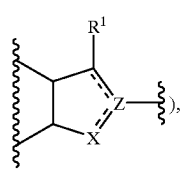

(Ic)

Z represents a carbon atom or a $CR^4$ group wherein $R^4$ represents a hydrogen atom or a linear or branched ($C_1$–$C_6$) alkyl group,
$R^1$, $R^2$, $R^3$, which may be the same or different, each represent a hydrogen atom or a linear or branched ($C_1$–$C_6$) alkyl group,
it being possible for the groups ($R^2$ and $R^4$) or ($R^1$ and $R^4$) to form a cyclopropane group,
$R^5$ represents a hydrogen atom, a linear or branched ($C_1$–$C_6$)alkyl group or a benzyl group,
the symbol

----- means that the bonds can be single or double, it being understood that the valency of the atoms is respected,
wherein alkyl is understood to mean a linear or branched alkyl group containing from 1 to 6 carbon atoms,
their tautomers, enantiomers and diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc..

Among the pharmaceutically acceptable bases there may be mentioned, without implying any limitation, sodium hydroxide, potassium hydroxide, triethylamine, tert-butylamine etc..

Preferred compounds of the invention are compounds of formula (I) wherein $R^5$ represents a hydrogen atom.

Preferred rings B are those represented by formula (Ia).

Advantageously, the invention relates to compounds of formula (I) wherein $R^1$ and $R^2$ each simultaneously represent a hydrogen atom, $R^3$ represents a hydrogen atom or a methyl group, Z represents a carbon atom or a CH or C—CH$_3$ group, or ($R^1$ and $R^4$) or ($R^2$ and $R^4$) represent a cyclopropane group.

Preferred ring systems

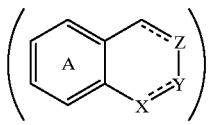

are 3,4-dihydronaphthalene, 1,2,3,4-tetrahydro-naphthalene, indane, indene or benzofuran. More specifically, the invention relates to 3,4-dihydronaphthalene, 1,2,3,4-tetrahydronaphthalene, indane, indene or benzofuran compounds unsubstituted or substituted by one or more identical or different substituents selected from halogen atoms and methyl, methoxy and CF$_3$ groups.

Even more preferably, the invention relates to compounds of formula (I) that are:

4-(3,4-dihydro-2-naphthylmethyl)-4,5-dihydro-1H-imidazole

4-[(8-chloro-3,4-dihydro-2-naphthyl)methyl]-4,5-dihydro-1H-imidazole 4-(benzo[b]furan-2-ylmethyl)-4,5-dihydro-1H-imidazole 4-{spiro[cyclopropan-2:2'-(1',2',3',4'-tetrahydronaphth)]-1-yl}-4,5-dihydro-1H-imidazole (isomer 1), 4-{spiro[cyclopropan-2:2'-(1',2',3',4'-tetrahydronaphth)]-1-yl}-4,5-dihydro-1H-imidazole (isomer 2), 4-[1,2,3,4-tetrahydro-2-naphthylmethyl]-4,5-dihydro-1H-imidazole (isomer 1), 4-[1,2,3,4-tetrahydro-2-naphthylmethyl]-4,5-dihydro-1H-imidazole (isomer 2), 4-[1,2,3,4-tetrahydro-2-naphthylmethyl]-4,5-dihydro-1H-imidazole (isomer 3), 4-[1,2,3,4-tetrahydro-2-naphthylmethyl]-4,5-dihydro-1H-imidazole (isomer 4), 4-(1,3-dihydro-1H-2-indenylmethyl)-4,5-dihydro-1H-imidazole, 4-[(5-fluoro-2,3-dihydro-1H-inden-2-yl)methyl-4,5-dihydro-1H-imidazole, 4-[(5,6-difluoro-2,3-dihydro-1H-inden-2-yl)methyl-4,5-dihydro-1H-imidazole, 4-[(7-fluoro-3,4-dihydro-2-naphthyl)methyl]-4,5-dihydro-1H-imidazole, 4-[(8-methoxy-3,4-dihydro-2-naphthyl)methyl]-4,5-dihydro-1H-imidazole, 4-[(3,4-dihydro-4,4-dimethyl-2-naphthyl)methyl]-4,5-dihydro-1H-imidazole, 4-[(8-chloro-2-naphthyl)methyl]-4,5-dihydro-1H-imidazole, 4-{spiro[cyclopropan-2':2"-(5",6"-difluoro-indan)]-1'-yl}-4,5-dihydro-1H-imidazole (diastereoisomer 1), 4-{spiro[cyclopropan-2':2"-(5",6"-difluoro-indan)]-1'-yl}-4,5-dihydro-1H-imidazole (diastereoisomer 2).

The tautomers, enantiomers and diastereoisomers and addition salts with a pharmaceutically acceptable acid or base of the preferred compounds of the invention form an integral part of the invention.

The present invention relates also to a process for the preparation of compounds of formula (I), characterised in that there is used as starting material a compound of formula (II):

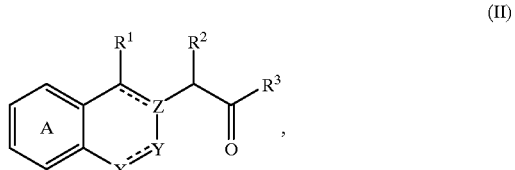

wherein A, X, Y, Z, $R^1$, $R^2$, $R^3$ and the symbol

----- are as defined hereinbefore, which is subjected either to the conditions of a Strecker reaction (KCN, NH$_4$Cl) or to the action of an amine $R_aNH_2$ (wherein $R_a$ represents a hydrogen atom or a hindered protecting group allowing better separation, where applicable, of the diastereoisomers formed) and of trimethylsilyl cyanide to yield a compound of formula (III):

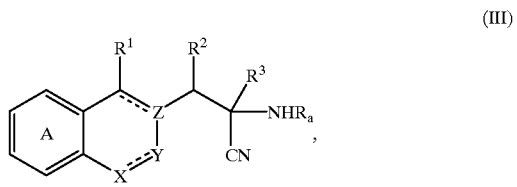

wherein A, X, Y, Z, $R^1$, $R^2$, $R^3$, $R_a$ and the symbol

----- are as defined hereinbefore, which compound of formula (III), when $R_a$ represents a hydrogen atom, may alternatively be obtained starting from a compound of formula (IV):

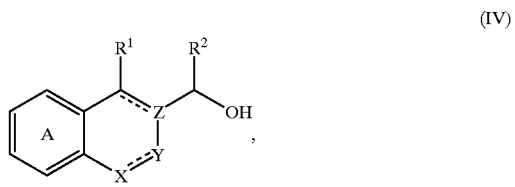

wherein A, X, Y, Z, $R^1$, $R^2$ and the symbol

----- are as defined hereinbefore, which is subjected to a halogenating agent to yield a compound of formula (V):

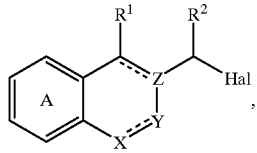
(V)

wherein A, X, Y, Z, $R^1$, $R^2$ and the symbol

----- are as defined hereinbefore and Hal represents a halogen atom, with which there is condensed a compound of formula (VI):

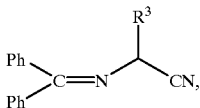
(VI)

wherein $R^3$ is as defined hereinbefore, to yield a compound of formula (VII):

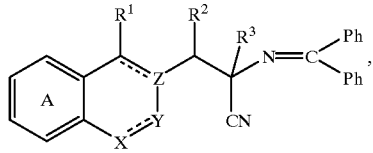
(VII)

wherein A, X, Y, Z, $R^1$, $R^2$, $R^3$ and the symbol

----- are as defined hereinbefore, which is subjected to acid hydrolysis to yield a compound of formula (III/a), a particular case of the compounds of formula (III):

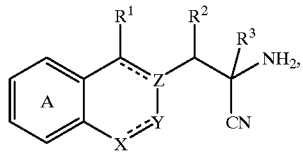
(III/a)

wherein A, X, Y, Z, $R^1$, $R^2$, $R^3$ and the symbol

----- are as defined hereinbefore, which compound of formula (III) is subjected to the action of a reducing agent such as $LiAlH_4$, $AlH_3$ or a catalytic hydrogenation, for example, to obtain a compound of formula (VIII):

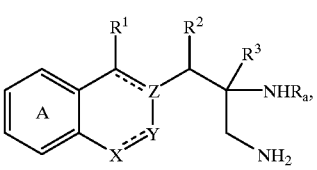
(VIII)

wherein A, X, Y, Z, $R^1$, $R^2$, $R^3$, $R_a$ and the symbol

----- are as defined hereinbefore, which, in the case where $R_a$ is other than a hydrogen atom, is deprotected in an acidic or reductive medium, for example, to yield a compound of formula (IX):

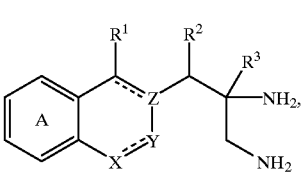
(IX)

wherein A, X, Y, Z, $R^1$, $R^2$, $R^3$ and the symbol

----- are as defined hereinbefore, which is reacted with formamidine acetate or methyl orthoformate to give a compound of formula (I/a), a particular case of the compounds of formula (I):

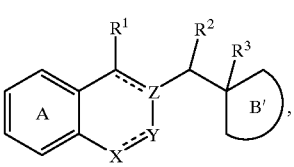
(I/a)

wherein A, X, Y, Z, $R^1$, $R^2$, $R^3$ and the symbol

----- are as defined hereinbefore and B' represents an unsubstituted imidazoline ring as represented in formula (Ia/a) or (Ib/a):

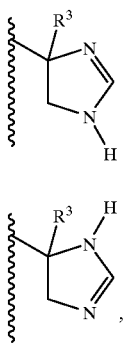
(Ia/a)

(Ib/a)

which can be subjected, in the presence of a basic system, to the action of a compound of formula (X):

$R^5_a$-J  (X), wherein $R^5_a$ represents a linear or branched ($C_1$–$C_6$)alkyl group or a benzyl group and J represents a leaving group such as a halogen atom or a tosyl group, to obtain a compound of formula (I/b), a particular case of the compounds of formula (I):

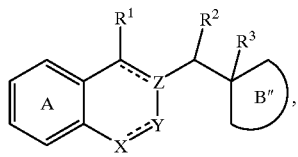
(I/b)

wherein A, X, Y, Z, $R^1$, $R^2$, $R^3$ and the symbol

----- are as defined hereinbefore and B" represents a substituted imidazoline ring as represented in formula (Ia/b) or (Ib/b):

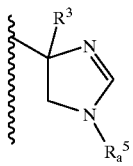
(Ia/b)

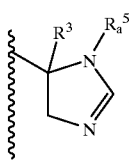
(Ib/b)

wherein $R^5_a$ is as defined hereinbefore,
which compounds (I/a) and (I/b) constitute the totality of the compounds of formula (I) and may be purified according to a conventional separation technique, are converted, if desired, into their addition salts with a pharmaceutically acceptable acid or base and are separated, where appropriate, into their isomers according to a conventional separation technique.

The present invention relates also to a process for the preparation of compounds of formula (I/a), characterised in that there is used as starting material a compound of formula (II'):

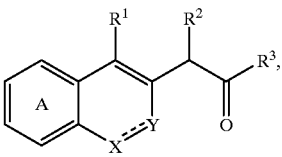
(II')

wherein A, X, Y, $R^1$, $R^2$, $R^3$ and the symbol

----- are as defined hereinbefore,
which is condensed with a chiral amine compound of formula (XI):

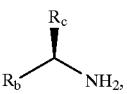
(XI)

wherein $R_b$ and $R_c$, which are different, represent an alkyl or aryl group,
to obtain a compound of formula (XII):

(XII)

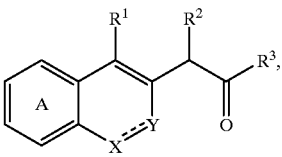

wherein A, X, Y, $R^1$, $R^2$, $R^3$, $R_b$, $R_c$ and the symbol

----- are as defined hereinbefore,
which is subjected to the action of N-1-isocyano-cyclohexene and benzoic acid to yield a compound of formula (XIII):

(XIII)

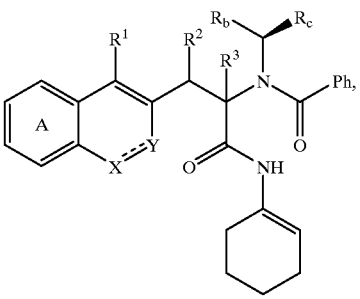

wherein A, X, Y, $R^1$, $R^2$, $R^3$, $R_b$, $R_c$ and the symbol

----- are as defined hereinbefore, which compound of formula (XIII) is chromatographed on silica to yield the diastereoisomers of formulae (XIII$_a$) and (XIII$_b$):

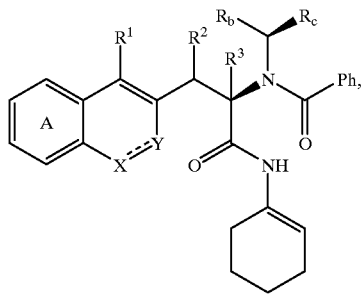

(XIII$_a$)

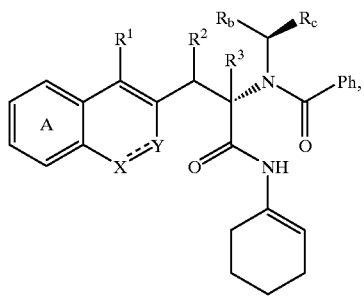

(XIII$_b$)

wherein A, X, Y, $R^1$, $R^2$, $R^3$, $R_b$, $R_c$ and the symbol

----- are as defined hereinbefore, which compound of formula (XIII$_a$) is subjected to the action of $H_3O^+$ to obtain a compound of formula (XIV$_a$):

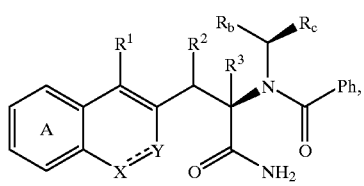

(XIV$_a$)

wherein A, X, Y, $R^1$, $R^2$, $R^3$, $R_b$, $R_c$ and the symbol

----- are as defined hereinbefore, which is subjected to catalytic hydrogenation to yield a compound of formula (XV$_a$):

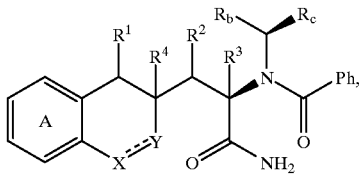

(XV$_a$)

wherein A, X, Y, $R^1$, $R^2$, $R^3$, $R^4$, $R_b$, $R_c$ and the symbol

----- are as defined hereinbefore, which compound of formula (XV$_a$) is chromatographed on silica to yield the diastereoisomers of formulae (XV$_a$') and (XV$_a$"):

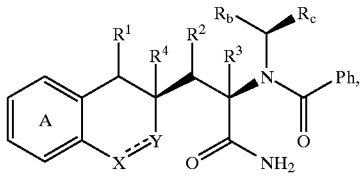

(XV$_a$')

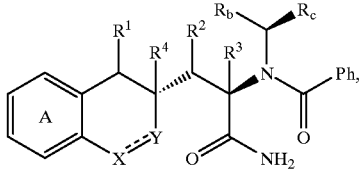

(XV$_a$")

wherein A, X, Y, $R^1$, $R^2$, $R^3$, $R^4$, $R_b$, $R_c$ and the symbol

----- are as defined hereinbefore, which compound of formula (XV$_a$') is subjected, in succession, to the action of a reducing agent such as $BH_3$ and then to hydrogenolysis to yield a compound of formula (XVI$_a$'):

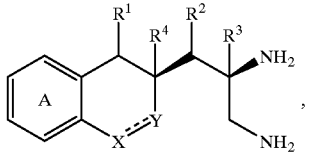

(XVI$_a$')

wherein A, X, Y, $R^1$, $R^2$, $R^3$, $R^4$ and the symbol

----- are as defined hereinbefore,
which is reacted with formamidine acetate or methyl orthoformate to obtain a compound of formula (XVII$_a$'), a particular case of the compounds of formula (I/a):

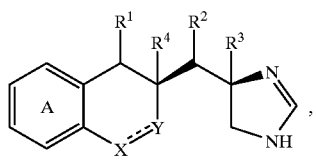

(XVII$_a$')

wherein A, X, Y, R$^1$, R$^2$, R$^3$, R$^4$ and the symbol

----- are as defined hereinbefore, it being possible, using the same reaction sequence, to obtain:

a compound of formula (XVII$_a$"), a particular case of the compounds of formula (I/a), obtained starting from the diastereoisomer (XV$_a$"):

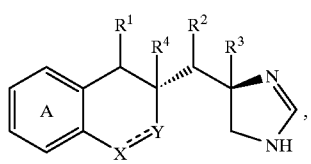

(XVII$_a$")

wherein A, X, Y, R$^1$, R$^2$, R$^3$, R$^4$ and the symbol

----- are as defined hereinbefore, a compound of formula (XVII$_b$'), a particular case of the compounds of formula (I/a), obtained starting from the diastereoisomer (XIII$_b$):

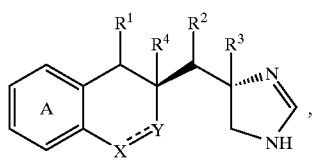

(XVII$_b$')

wherein A, X, Y, R$^1$, R$^2$, R$^3$, R$^4$ and the symbol

----- are as defined hereinbefore, a compound of formula (XVII$_b$"), a particular case of the compounds of formula (I/a), obtained starting from the diastereoisomer (XIII$_b$):

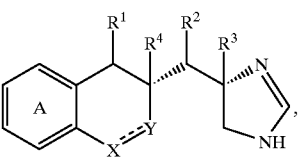

(XVII$_b$")

wherein A, X, Y, R$^1$, R$^2$, R$^3$, R$^4$ and the symbol

----- are as defined hereinbefore, or which compound of formula (XIV$_a$) is subjected, in succession, to the action of a reducing agent such as BH$_3$ and then to hydrogenolysis to yield a compound of formula (XVIII$_a$):

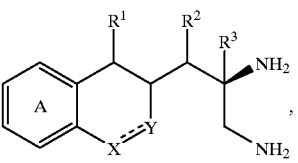

(XVIII$_a$)

wherein A, X, Y, R$^1$, R$^2$, R$^3$ and the symbol

----- are as defined hereinbefore, which is reacted with formamidine acetate or methyl orthoformate to obtain a compound of formula (XIX$_a$), a particular case of the compounds of formula (I/a):

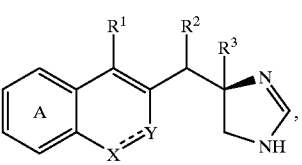

(XIX$_a$)

wherein A, X, Y, R$^1$, R$^2$, R$^3$ and the symbol

----- are as defined hereinbefore, it being possible, using the same reaction sequence, to obtain a compound of formula (XIX$_b$), a particular case of the compounds of formula (I/a), obtained starting from the corresponding compound (XIV$_b$):

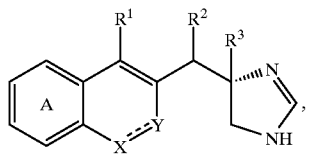

(XIX$_b$)

wherein A, X, Y, R$^1$, R$^2$, R$^3$ and the symbol

----- are as defined hereinbefore, which compounds of formulae (XVII$_a$'), (XVII$_a$"), (XVII$_b$'), (XVII$_b$"), (XIX$_a$) and (XIX$_b$) may be purified according to a conventional separation technique and converted, if desired, into their addition salts with a pharmaceutically acceptable acid or base.

The compounds of formulae (II) and (II') are obtained, for example:

starting from a compound of formula (XX):

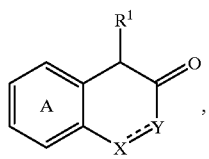

(XX)

wherein A, X, Y, R$^1$ and the symbol

----- are as defined hereinbefore, which is subjected to a Wittig-Horner reaction optionally followed by reduction to yield a compound of formula (XXI):

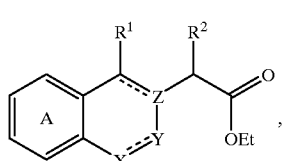

(XXI)

wherein A, X, Y, Z, R$^1$, R$^2$ and the symbol

----- are as defined hereinbefore, which is subjected to reduction to obtain a compound of formula (XXII), a particular case of the compounds of formula (II):

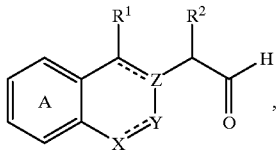

(XXII)

wherein A, X, Y, Z, R$^1$, R$^2$ and the symbol

----- are as defined hereinbefore, or which is subjected to a Wittig reaction optionally followed by reduction to yield a compound of formula (XXIII), a particular case of the compounds of formula (II):

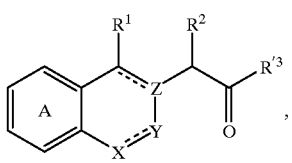

(XXIII)

wherein A, X, Y, Z, R$^1$, R$^2$ and the symbol

----- as defined hereinbefore and R'$^3$ represents a linear or branched (C$_1$–C$_6$)alkyl group, or starting from a compound of formula (XXIV):

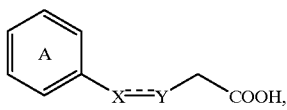

(XXIV)

wherein A, X, Y and the symbol

----- are as defined hereinbefore, which is cyclised (after conversion into the corresponding acid chloride) in the presence of AlCl$_3$ to yield a compound of formula (XXV):

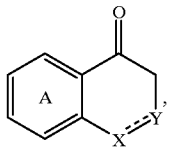

(XXV)

wherein A, X, Y and the symbol

----- are as defined hereinbefore, with which there is condensed, in a basic medium, diethyl chlorophosphate to yield a compound of formula (XXVI):

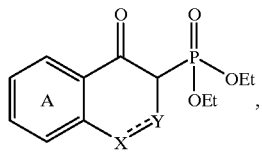
(XXVI)

wherein A, X, Y and the symbol

----- are as defined previously, with which there is condensed the compound of formula (XXVII):

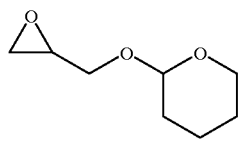
(XXVII)

to yield a compound of formula (XXVIII):

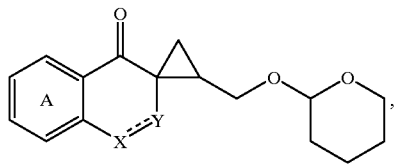
(XXVIII)

wherein A, X, Y and the symbol

----- are as defined hereinbefore, which is subjected to the action of a reductive system to yield a compound of formula (XXIX):

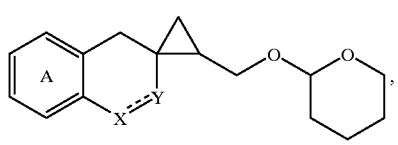
(XXIX)

wherein A, X, Y and the symbol

----- are as defined hereinbefore, which may be hydrolysed under the conditions of the reaction or isolated and hydrolysed in a subsequent step to give a compound of formula (XXX):

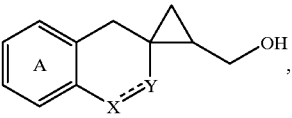
(XXX)

wherein A, X, Y and the symbol

----- are as defined hereinbefore, or which compound of formula (XXV) is subjected to the action of ethyl 2-[(diethoxyphosphoryl)oxy]acrylate in a basic medium to yield a compound of formula (XXXI):

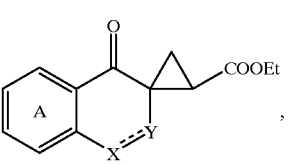
(XXXI)

wherein A, X, Y and the symbol

----- are as defined hereinbefore, which is placed in the presence of a reducing agent such as NaBH$_3$CN and a Lewis acid such as zinc iodide to obtain a compound of formula (XXXII):

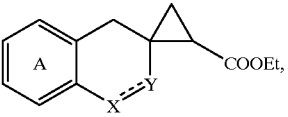
(XXXII)

wherein A, X, Y and the symbol

----- are as defined hereinbefore, which is subjected to the action of a reducing agent such as LiAlH$_4$ to yield a compound of formula (XXVIII), which is oxidised to obtain a compound of formula (X=II), a particular case of the compounds of formula (II):

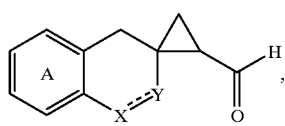

(XXXIII)

wherein A, X, Y and the symbol

----- are as defined hereinbefore.

The compounds of the invention and the pharmaceutical compositions comprising them have proved to be of use in the treatment of depression.

In fact, the compounds of the present invention are specific α2-adrenergic antagonists and also act as powerful inhibitors of serotonin and noradrenaline reuptake.

As such, they may be used therapeutically in the treatment of depression, obesity, panic attacks, anxiety, obsessive-compulsive disorders, cognitive disorders, phobias, impulsive disorders associated with the abuse of drugs and withdrawal therefrom, sexual dysfunctions and Parkinson's disease.

The present invention relates also to pharmaceutical compositions comprising at least one compound of formula (I) on its own or in combination with one or more pharmaceutically acceptable excipients.

Among the pharmaceutical compositions according to the invention, there may be mentioned more especially those that are suitable for oral, parenteral, nasal, per- or trans-cutaneous, rectal, perlingual, ocular or respiratory administration, and especially tablets or dragées, sublingual tablets, sachets, paquets, gelatin capsules, glossettes, lozenges, suppositories, creams, ointments, dermal gels and drinkable or injectable ampoules.

The dosage used varies according to the sex, age and weight of the patient, the route of administration, the nature of the therapeutic indication, and any associated treatments, and ranges from 1 mg to 1000 mg per 24 hours in 1 or more administrations.

The following Examples illustrate the invention but do not limit it in any way.

The nomenclature adopted for the following Examples is substitution in the 4-position of the imidazoline ring but the Examples also include the tautomers substituted in the 5-position. By way of example, the compound of Example 1 (4-(3,4-dihydro-2-naphthylmethyl)-4,5-dihydro-1H-imidazole fumarate) can also be written 5-(3,4-dihydro-2-naphthylmethyl)-4,5-dihydro-1H-imidazole fumarate.

EXAMPLE 1

4-(3,4-Dihydro-2-naphthylmethyl)-4,5-dihydro-1H-imidazole fumarate

Step 1: Ethyl 2-(3,4-dihydro-naphth-2-yl)acetate

A solution of 56 g (0.25 mol) of triethyl phosphonoacetate in 70 ml of tetrahydrofuran (THF) is added dropwise to a suspension, maintained at 0° C., of 6 g (0.25 mol) of NaH in 600 ml of anhydrous THF under a nitrogen atmosphere. The mixture is then stirred at 10° C. for 30 minutes, cooled to 0° C., and then treated, dropwise, with a solution of 36.52 g (0.25 mol) of β-tetralone in 50 ml of anhydrous THF. After stirring for 3 hours at 20° C., the mixture is hydrolysed, at 0° C., with 200 ml of water. The solvent is evaporated off under reduced pressure and the residue is extracted with dichloromethane ($CH_2Cl_2$)(3×200 ml). The combined organic phases are washed with saturated NaCl solution, dried and concentrated to yield an oily brown residue. Distillation under a partial vacuum allows the title compound to be obtained in the form of a colourless liquid.

Boiling point (0.03mm Hg): 88–91° C.

Elemental Microanalysis

|  | C % | H % |
| --- | --- | --- |
| Theoretical: | 77.75 | 7.46 |
| Found: | 77.59 | 7.57 |

Step 2: 2-(3,4-Dihydro-naphth-2-yl)acetaldehyde

A solution, cooled to −60° C., of 18.60 g (0.086 mol) of the ester obtained in Step 1 in 360 ml of $CH_2Cl_2$ is treated, dropwise, with a molar solution of diisobutylaluminium hydride in $CH_2Cl_2$ (170 ml). After stirring for 2 hours at −60° C., the mixture is hydrolysed, at that temperature, by successive addition of $NH_4Cl$ 10% (35 ml) and 1N HCl (42 ml). The temperature of the mixture is increased to 20° C. over a period of 1 hour and the precipitate formed is then suctioned off and washed with $CH_2Cl_2$. The filtrate is washed with water and then with saturated NaCl solution, dried and evaporated. The oily residue obtained is chromatographed on silica, eluting with a mixture of cyclohexane/EtOAc=95/5. The expected compound is isolated in the form of a colourless oil and is used as such for the following reaction.

Step 3: 2-Amino-3-(3,4-dihydro-naphth-2-yl)propionitrile

To a solution of 3.44 g (20 mmol) of the aldehyde obtained in Step 2 in 100 ml of $CH_2Cl_2$ there are added, in succession, at 20° C., 0.25 g of $ZnI_2$ and then, slowly, 2.18 g (22 mmol) of trimethylsilyl cyanide. After stirring for 20 hours at 20° C., the mixture is concentrated in vacuo. The residue obtained is treated with 200 ml of a solution of $NH_3$ in $CH_3OH$ (7N); the mixture is stirred for 4 hours in a stoppered receptacle and then concentrated in vacuo. The residue is taken up in 1N HCl and the suspension is washed with 50 ml of $Et_2O$; the aqueous phase is rendered alkaline with 6N NaOH and extracted with $CH_2Cl_2$ (3×50 ml). The combined organic phases are washed with saturated NaCl solution, dried and concentrated to yield the expected compound in the form of an oil, which is used directly for the following reaction.

Step 4: 3-(3,4-Dihydro-2-naphthyl)-propane-1,2-diamine

A mixture composed of 2.57 g (13 mmol) of the nitrile obtained in Step 3, 120 ml of $CH_3OH$, 2 g of Raney nickel and 50 ml of a solution of $NH_3$ in $CH_3OH$ (7N) is hydrogenated under a pressure of one atmosphere for 16 hours. After filtration over Celite, the solution is concentrated and the residue is chromatographed on silica, eluting with a mixture of $CH_2Cl_2/CH_3OH/NH_4OH$ conc.=90/10/1, to yield the expected compound in the form of a colourless oil.

Elemental Microanalysis

|  | C % | H % | N % |
|---|---|---|---|
| Theoretical: | 77.18 | 8.97 | 13.85 |
| Found: | 76.80 | 8.42 | 13.26 |

Step 5: 4-(3,4-Dihydro-2-naphthylmethyl)-4,5-dihydro-1H-imidazole fumarate

A mixture composed of 0.505 g (2.5 mmol) of the compound obtained in Step 4 and 0.286 g (2.75 mmol) of formamidine acetate in 20 ml of EtOH is stirred at 20° C. for 16 hours. After evaporating off the solvent, the residue is taken up in 10 ml of $CH_2Cl_2$; the mixture is treated with 5 ml of 2N NaOH and extracted with $CH_2Cl_2$ (3×20 ml). The combined organic phases are dried and concentrated; the residual oil is dissolved in 10 ml of EtOH and the mixture is treated with a solution of 0.29 g (2.5 mmol) of fumaric acid in 5 ml of EtOH. The title compound is isolated after recrystallisation.

Melting point: 165–166° C.

Elemental Microanalysis

|  | C % | H % | N % |
|---|---|---|---|
| Theoretical: | 65.84 | 6.14 | 8.53 |
| Found: | 66.01 | 6.13 | 8.41 |

Examples 2 and 3 are obtained after resolving the compound obtained in Step 4 of Example 1 by means of (+)-dibenzoyl-D-tartaric acid or (−)-dibenzoyl-L-tartaric acid by successive recrystallisations from MeOH and then neutralising the salt with 1N NaOH and extracting with $CH_2Cl_2$, and then proceeding as in Step 5 of Example 1.

EXAMPLE 2

(4R)-4-(3,4-dihydro-2-naphthylmethyl)-4,5-dihydro-1H-imidazole fumarate

Step 1: (2R)-3-(dihydro-2-naphthyl)-propane-1,2-diamine

Step 2.: (4R)-4-(3,4-dihydro-2-naphthylmethyl)-4,5-dihydro-1H-imidazole fumarate Melting point: 164–165° C.

Elemental Microanalysis

|  | C % | H % | N % |
|---|---|---|---|
| Theoretical: | 65.84 | 6.14 | 8.53 |
| Found: | 65.71 | 6.26 | 8.57 |

EXAMPLE 3

(4S)-4-(3,4-dihydro-2-naphthyl)-4,5-dihydro-1H-imidazole fumarate

Step 1: (2S)-3-(3,4-dihydro-2-naphthyl)-propane-1,2-diamine

Step 2: (4S)-4-(3,4-dihydro-2-naphthylmethyl)-4,5-dihydro-1H-imidazole fumarate

Melting point: 164–165° C.

Elemental Microanalysis

|  | C % | H % | N % |
|---|---|---|---|
| Theoretical: | 65.84 | 6.14 | 8.53 |
| Found: | 65.93 | 6.19 | 8.58 |

EXAMPLE 4

4[(6-Methyl-3,4-dihydro-2-naphthyl)methyl]-4,5-dihydro-1H-imidazole fumarate Step 1: Ethyl 2-(6-methyl-3,4-dihydro-naphth-2-yl) acetate The procedure is as in Step 1 of Example 1.

Boiling point (0.03mm Hg): 99–102° C.

Elemental Microanalysis

|  | C % | H % |
|---|---|---|
| Theoretical: | 78.23 | 7.88 |
| Found: | 78.63 | 8.06 |

Step 2: 3-(6-Methyl-3,4-dihydro-naphth-2-yl) propane-1,2-diamine

The procedure is as in Steps 2, 3 and 4 of Example 1.

Elemental Microanalysis

|  | C % | H % | N % |
|---|---|---|---|
| Theoretical: | 77.73 | 9.32 | 12.95 |
| Found: | 77.56 | 9.45 | 12.85 |

Step 3: 4-[(6-Methyl-3,4-dihydro-2-naphthyl)methyl]-4,5-dihydro-1H-imidazole fumarate Melting point: 177–178° C.

Elemental Microanalysis

|  | C % | H % | N % |
|---|---|---|---|
| Theoretical: | 66.65 | 6.48 | 8.18 |
| Found: | 66.30 | 6.65 | 8.12 |

EXAMPLE 5

4-[(7-Methyl-3,4-dihydro-2-naphthyl)methyl]-4,5-dihydro-1H-imidazole fumarate Step 1: Ethyl 2-(7-methyl-3,4-dihydro-naphth-2-yl) acetate The procedure is as in Step 1 of Example 1.
Boiling point (0.03mm Hg): 101–103° C.
Elemental Microanalysis

|  | C % | H % |
| --- | --- | --- |
| Theoretical: | 78.23 | 7.88 |
| Found: | 78.09 | 7.80 |

Step 2: 3-(7-Methyl-3,4-dihydro-naphth-2-yl) propane-1,2-diamine

The procedure is as in Steps 2, 3 and 4 of Example 1.
Elemental Microanalysis

|  | C % | H % | N % |
| --- | --- | --- | --- |
| Theoretical: | 77.73 | 9.32 | 12.95 |
| Found: | 78.06 | 9.23 | 12.44 |

Step 3: 4-[(7-Methyl-3,4-dihydro-2-naphthyl) methyl]-4,5-dihydro-1H-imidazole fumarate Melting point: 137–139° C.
Elemental Microanalysis

|  | C % | H % | N % |
| --- | --- | --- | --- |
| Theoretical: | 66.65 | 6.48 | 8.18 |
| Found: | 66.27 | 6.40 | 8.23 |

EXAMPLE 6

4-[(7-Methoxy-3,4-dihydro-2-naphthyl)methyl]-4,5-dihydro-1H-imidazole fumarate

Step 1: Ethyl 2-(7-methoxy-3,4-dihydro-naphth-2-yl)acetate

The procedure is as in Step 1 of Example 1.
Elemental Microanalysis

|  | C % | H % |
| --- | --- | --- |
| Theoretical: | 73.15 | 7.37 |
| Found: | 73.12 | 7.34 |

Step 2: 3-(7-Methoxy-3,4-dihydro-naphth-2-yl) propane-1,2-diamine

The procedure is as in Steps 2, 3 and 4 of Example 1.
Elemental Microanalysis

|  | C % | H % | N % |
| --- | --- | --- | --- |
| Theoretical: | 72.38 | 8.68 | 12.06 |
| Found: | 72.74 | 8.68 | 11.79 |

Step 3: 4-[(7-Methoxy-3,4-dihydro-2-naphthyl) methyl]-4,5-dihydro-1H-imidazole fumarate Melting point: 136–138° C.
Elemental Microanalysis

|  | C % | H % | N % |
| --- | --- | --- | --- |
| Theoretical: | 63.68 | 6.19 | 7.82 |
| Found: | 63.43 | 6.40 | 7.65 |

EXAMPLE 7

4-[(7-Fluoro-3,4-dihydro-2-naphthyl)methyl]-4,5-dihydro-1H-imidazole fumarate

Step 1: Ethyl 2-(7-fluoro-3,4-dihydro-naphth-2-yl) acetate

The procedure is as in Step 1 of Example 1.
Boiling point (0.02mm Hg): 92–94° C.
Elemental Microanalysis

|  | C % | H % |
| --- | --- | --- |
| Theoretical: | 71.78 | 6.45 |
| Found: | 72.07 | 6.63 |

Step 2: 3-(7-Fluoro-3,4-dihydro-naphth-2-yl) propane-1,2-diamine

The procedure is as in Steps 2, 3 and 4 of Example 1.
Elemental Microanalysis

|  | C % | H % | N % |
| --- | --- | --- | --- |
| Theoretical: | 70.88 | 7.78 | 12.72 |
| Found: | 70.97 | 7.59 | 12.56 |

Step 3: 4-[(7-Fluoro-3,4-dihydro-2-naphthyl) methyl]-4,5-dihydro-1H-imidazole fumarate Melting point: 155–157° C.
Elemental Microanalysis

|  | C % | H % | N % |
| --- | --- | --- | --- |
| Theoretical: | 62.42 | 5.53 | 8.09 |
| Found: | 62.27 | 5.77 | 8.06 |

EXAMPLE 8

4-[7-Trifluoromethyl-3,4-dihydro-2-naphthyl)methyl]-4,5-dihydro-1H-imidazole fumarate Step 1: Ethyl 2-(7-trifluoromethyl-3,4-dihydro-naphth-2-yl)acetate The procedure is as in Step 1 of Example 1.

Elemental Microanalysis

|  | C % | H % |
|---|---|---|
| Theoretical: | 63.38 | 5.32 |
| Found: | 63.61 | 5.73 |

Step 2: 3-(7-Trifluoromethyl-3,4-dihydro-naphth-2-yl)propane-1,2-diamine

The procedure is as in Steps 2, 3 and 4 of Example 1.

Elemental Microanalysis

|  | C % | H % | N % |
|---|---|---|---|
| Theoretical: | 62.21 | 6.34 | 10.36 |
| Found: | 62.28 | 6.18 | 10.34 |

Step 3: 4-[7-Trifluoromethyl-3,4-dihydro-2-naphthyl)methyl]-4,5-dihydro-1H-imidazole fumarate Melting point: 169–171° C.

Elemental Microanalysis

|  | C % | H % | N % |
|---|---|---|---|
| Theoretical: | 57.78 | 4.83 | 7.07 |
| Found: | 57.72 | 5.25 | 7.03 |

EXAMPLE 9

4-[(8-Fluoro-3,4-dihydro-2-naphthyl)methyl]-4,5-dihydro-1H-imidazole fumarate

Step 1: Ethyl 2-(8-fluoro-3,4-dihydro-naphth-2-yl)acetate

The procedure is as in Step 1 of Example 1.

Elemental Microanalysis

|  | C % | H % |
|---|---|---|
| Theoretical: | 71.78 | 6.45 |
| Found: | 71.67 | 6.73 |

Step 2: 3-(8-Fluoro-3,4-dihydro-naphth-2-yl)propane-1,2-diamine

The procedure is as in Steps 2, 3 and 4 of Example 1.

Elemental Microanalysis

|  | C % | H % | N % |
|---|---|---|---|
| Theoretical: | 70.88 | 7.78 | 12.72 |
| Found: | 71.05 | 7.86 | 12.48 |

Step 3: 4-[(8-Fluoro-3,4-dihydro-2-naphthyl)methyl]-4,5-dihydro-1H-imidazole fumarate Melting point: 183–185° C.

Elemental Microanalysis

|  | C % | H % | N % |
|---|---|---|---|
| Theoretical: | 62.42 | 5.53 | 8.09 |
| Found: | 62.24 | 5.63 | 8.04 |

EXAMPLE 10

4-[(8-Chloro-3,4-dihydro-2-naphthyl)methyl]-4,5-dihydro-1H-imidazole fumarate

Step 1: Ethyl 2-(8-chloro-3,4-dihydro-naphth-2-yl)acetate

The procedure is as in Step 1 of Example 1.

Boiling point (0.02mm Hg): 112–114° C.

Step 2: 3-(8-Chloro-3,4-dihydro-naphth-2-yl)propane-1,2-diamine

The procedure is as in Steps 2, 3 and 4 of Example 1.

Elemental Microanalysis

|  | C % | H % | N % | Cl % |
|---|---|---|---|---|
| Theoretical: | 65.95 | 7.24 | 11.83 | 14.97 |
| Found: | 65.72 | 7.05 | 11.92 | 14.96 |

Step 3: 4-[(8-Chloro-3,4-dihydro-2-naphthyl)methyl]-4,5-dihydro-1H-imidazole fumarate Melting point: 191–195° C.

Elemental Microanalysis

|  | C % | H % | N % | Cl % |
|---|---|---|---|---|
| Theoretical: | 59.59 | 5.28 | 7.72 | 9.77 |
| Found: | 59.55 | 5.36 | 7.66 | 9.89 |

EXAMPLE 11

4-[(8-Methyl-3,4-dihydro-2-naphthyl)methyl]-4,5-dihydro-1H-imidazole fumarate

Step 1: Ethyl 2-(8-methyl-3,4-dihydro-naphth-2-yl)acetate

The procedure is as in Step 1 of Example 1.

Boiling point (0.02mm Hg): 95–97° C.

Step 2: 3-(8-Methyl-3,4-dihydro-naphth-2-yl)propane-1,2-diamine

The procedure is as in Steps 2, 3 and 4 of Example 1.

Elemental Microanalysis

|  | C % | H % | N % |
|---|---|---|---|
| Theoretical: | 77.73 | 9.32 | 12.95 |
| Found: | 77.94 | 9.17 | 12.65 |

Step 3: 4-[(8-Methyl-3,4-dihydro-2-naphthyl)methyl]-4,5-dihydro-1H-imidazole fumarate Melting point: 182–184° C.

Elemental Microanalysis

|  | C % | H % | N % |
|---|---|---|---|
| Theoretical: | 66.65 | 6.49 | 8.18 |
| Found: | 66.08 | 6.44 | 7.98 |

EXAMPLE 12

4-[(8-Methoxy-3,4-dihydro-2-naphthyl)methyl]-4,5-dihydro-1H-imidazole fumarate

Step 1: Ethyl 2-(8-methoxy-3,4-dihydro-naphth-2-yl)acetate

The procedure is as in Step 1 of Example 1.

Elemental Microanalysis

|  | C % | H % |
|---|---|---|
| Theoretical: | 73.15 | 7.37 |
| Found: | 73.50 | 7.34 |

Step 2: 3-(8-Methoxy-3,4-dihydro-naphth-2-yl)propane-1,2-diamine

The procedure is as in Steps 2, 3 and 4 of Example 1.

Elemental Microanalysis

|  | C % | H % | N % |
|---|---|---|---|
| Theoretical: | 72.38 | 8.68 | 12.06 |
| Found: | 72.67 | 8.49 | 11.96 |

Step 3: 4-[(8-Methoxy-3,4-dihydro-2-naphthyl)methyl]-4,5-dihydro-1H-imidazole fumarate Melting point: 206–208° C.

Elemental Microanalysis

|  | C % | H % | N % |
|---|---|---|---|
| Theoretical: | 63.68 | 6.19 | 7.82 |
| Found: | 63.00 | 6.26 | 7.43 |

EXAMPLE 13

4-(2H-3-Chromenylmethyl)-4,5-dihydro-1H-imidazole

Step 1: 3-(2H-3-Chromenyl)-1,2-propanediamine

The procedure is as in Steps 1,2, 3 and 4 of Example 1.

Elemental Microanalysis

|  | C % | H % | N % |
|---|---|---|---|
| Theoretical: | 70.56 | 7.90 | 13.72 |
| Found: | 70.28 | 7.77 | 13.85 |

Step 2: 4-(2H-3-Chromenylmethyl)-4,5-dihydro-1H-imidazole

Melting point: 148–150° C.

Elemental Microanalysis

|  | C % | H % | N % |
|---|---|---|---|
| Theoretical: | 61.81 | 5.49 | 8.48 |
| Found: | 61.57 | 5.60 | 8.50 |

EXAMPLE 14

4-(3,4-Dihydro-2-naphthylmethyl)-4-methyl-4,5-dihydro-1H-imidazole fumarate

Step 1: 2-Amino-2-methyl-3-(3,4-dihydro-naphth-2-yl)propionitrile

To a solution of 6.50 g (35 mmol) of 1-(3,4-dihydronaphth-2-yl)propan-2-one in a mixture of 41 ml of $CH_3OH$ and 20 ml of water there are added, in succession, all at once, 2.34 g (36 mmol) of KCN and 1.93 g (36 mmol) of $NH_4Cl$. After stirring for 72 hours at 20° C., the mixture is diluted with $H_2O$ and extracted with $CH_2Cl_2$ (4×50 ml). The solvents are evaporated off; the residue is taken up in $Et_2O$ and extracted again with 1N HCl (3×40 ml). The combined aqueous phases are rendered alkaline with 6N NaOH and then extracted with $CH_2Cl_2$ (3×50 ml). After drying and concentrating the organic phases, the title compound is obtained in the form of a yellow oil, which is used directly for the following reaction.

Step 2: 3-(3,4-Dihydro-naphth-2-yl)-2-methyl-propane-1,2-diamine

A solution of 5 g (23.6 mmol) of the compound obtained in the previous Step in 20 ml of anhydrous THF is added dropwise to a suspension of 1.90 g (50 mmol) of LiAlH$_4$ in 50 ml of anhydrous THF, whilst maintaining the temperature below 10° C. After stirring for 1 hour at 20° C., the mixture is cooled to 0° C. and hydrolysed by successive addition of 11 ml of isopropanol and 11 ml of saturated NaCl solution. The precipitate formed is suctioned off and rinsed with THF; the filtrate is concentrated in vacuo and the residue is taken up in 1N HCl (50 ml) and then washed with ether (10 ml). The aqueous phase is rendered basic with 6N NaOH and extracted with CH$_2$Cl$_2$ (3×50 ml). The organic phases are dried and concentrated and the residue obtained is chromatographed on silica, with a mixture of CH$_2$Cl$_2$/CH$_3$OH/NH$_4$OH conc.=90/10/1 as eluant. The title compound is isolated in the form of an oil.

Step3: 4-(3,4-Dihydro-2-naphthylmethyl)-4-methyl-4,5-dihydro-1H-imidazole fumarate The procedure is as in Step 5 of Example 1, starting from the compound obtained in Step 2.

Melting point: 146–148° C.

Elemental Microanalysis

|  | C % | H % | N % |
|---|---|---|---|
| Theoretical: | 66.65 | 6.48 | 8.18 |
| Found: | 66.24 | 6.50 | 8.14 |

EXAMPLE 15

4-[(3,4-Dihydro-4,4-dimethyl-2-naphthyl)methyl]-4,5-dihydro-1H-imidazole hemi-fumarate The procedure is as in Example 14, starting from (4,4-dimethyl-3,4-dihydronaphth-2-yl)acetaldehyde.

Melting point: 178–179° C.

Elemental Microanalysis

|  | C % | H % | N % |
|---|---|---|---|
| Theoretical: | 71.86 | 7.36 | 9.21 |
| Found: | 71.93 | 7.40 | 9.13 |

EXAMPLE 16

4-[1,2,3,4-Tetrahydro-2-naphthylmethyl]-4,5-dihydro-1H-imidazole fumarate

Step 1: Ethyl (1,2,3,4-tetrahydro-naphth-2-yl) acetate

A mixture of 26 g (0.12 mol) of the ester obtained in Step 1 of Example 1 and 2.50 g of Pd/C 10% in 250 ml of EtOH is hydrogenated under 1 bar, at 20° C., overnight. After filtering off the catalyst and washing with ethanol, the filtrate is concentrated in vacuo to yield the expected compound in the form of a colourless oil.

Boiling point (0.02mm Hg): 90–94° C.

Elemental Microanalysis

|  | C % | H % |
|---|---|---|
| Theoretical: | 77.03 | 8.31 |
| Found: | 77.49 | 8.16 |

Step 2: (1,2,3,4-Tetrahydro-naphth-2-yl) acetaldehyde

The procedure is as in Step 2 of Example 1, starting from the compound obtained in Step 1.

Elemental Microanalysis

|  | C % | H % |
|---|---|---|
| Theoretical: | 82.72 | 8.10 |
| Found: | 82.89 | 7.98 |

Step 3: 3-(1,2,3,4-Tetrahydro-naphth-2-yl)propane-1,2-diamine

The procedure is as in Steps 3 and 4 of Example 1, starting from the compound obtained in Step 2.

Elemental Microanalysis

|  | C % | H % | N % |
|---|---|---|---|
| Theoretical: | 76.42 | 9.87 | 13.71 |
| Found: | 76.10 | 9.76 | 13.95 |

Step 4: 4-[1,2,3,4-Tetrahydro-2-naphthylmethyl]4,5-dihydro-1H-imidazole fumarate The procedure is as in Step 5 of Example 1, starting from the compound obtained in Step 3.

Melting point: 158–159° C.

Elemental Microanalysis

|  | C % | H % | N % |
|---|---|---|---|
| Theoretical: | 65.44 | 6.71 | 8.48 |
| Found: | 65.66 | 6.82 | 8.52 |

EXAMPLE 17

4-[1,2,3,4-Tetrahydro-2-naphthylmethyl]-4,5-dihydro-1H-imidazole fumarate (isomer 1)

Step 1: 4-(1,2,3,4-Tetrahydro-2-naphthylmethyl)-1-trityl-4,5-dihydro-1H-imidazole 1.25 ml (9 mmol) of triethylamine and 2.36 g (8.50 mmol) of trityl chloride are added, in succession, at 20° C., to a solution of the compound obtained in Example 16 (Step 4) in the form of the free amine (1.80 g, 8.40 mmol) in 50 ml of benzene, under nitrogen. After stirring for 15 hours at 20° C., the mixture is washed with H$_2$O, and the organic phase is dried and concentrated in vacuo to yield an oily residue. Chromatography on a chiral column, eluting with a solution of triethylamine in toluene (0.5%), allows the 4 isomers to be separated in the form of white solids.

Step 2: 4-[1,2,3,4-Tetrahydro-2-naphthylmethyl]-4,5-dihydro-1H-imidazole fumarate (isomer 1)

A solution of one of the isomers obtained in Step 1 (550 mg, 1.2 mmol) in a mixture of AcOH/H$_2$O=90/1 is heated at reflux for 2 hours 30 minutes. After cooling, the mixture is concentrated in vacuo; the residue is taken up in CH$_2$Cl$_2$ (10 ml) and treated with 1N NaOH solution. The organic phase is washed with saturated NaCl solution, dried and evaporated to yield an oily residue, which is chromatographed on silica, eluting with a mixture of CH$_2$Cl$_2$/CH$_3$OH/NH$_4$OH= 90/10. The oil obtained (170 mg, 0.8 mmol) is dissolved in EtOH and treated with 93 mg (0.8 mmol) of fumaric acid dissolved in 5 ml of EtOH. After concentration of the solution and recrystallisation from iPrOH, the title compound is obtained in the form of colourless prismatic crystals.

Melting point: 155–156° C.
Elemental Microanalysis

|  | C % | H % | N % |
| --- | --- | --- | --- |
| Theoretical: | 65.44 | 6.71 | 8.48 |
| Found: | 65.24 | 6.92 | 8.53 |

Examples 18 to 20 are obtained by proceeding as in Step 2 of Example 17, starting from the other isomers:

EXAMPLE 18

4-[1,2,3,4-Tetrahydro-2-naphthylmethyl]-4,5-dihydro-1H-imidazole fumarate (isomer 2)

Melting point: 155° C.
Elemental Microanalysis:

|  | C % | H % | N % |
| --- | --- | --- | --- |
| Theoretical: | 65.44 | 6.71 | 8.48 |
| Found: | 65.28 | 6.90 | 8.41 |

EXAMPLE 19

4-[1,2,3,4-Tetrahydro-2-naphthylmethyl]-4,5-dihydro-1H-imidazole fumarate (isomer 3)

Melting point: 159° C.
Elemental Microanalysis

|  | C % | H % | N % |
| --- | --- | --- | --- |
| Theoretical: | 65.44 | 6.71 | 8.48 |
| Found: | 65.69 | 7.01 | 8.49 |

EXAMPLE 20

4-[1,2,3,4-Tetrahydro-2-naphthylmethyl]-4,5-dihydro-1H-imidazole fumarate (isomer 4)

Melting point: 159° C.
Elemental Microanalysis

|  | C % | H % | N % |
| --- | --- | --- | --- |
| Theoretical: | 65.44 | 6.71 | 8.48 |
| Found: | 64.92 | 7.01 | 8.48 |

EXAMPLE 21

4-(1H-Inden-2-ylmethyl)-4,5-dihydro-1H-imidazole fumarate

The procedure is as in Example 1, starting from 2-indanone.

Melting point: 161–162° C.
Elemental Microanalysis

|  | C % | H % | N % |
| --- | --- | --- | --- |
| Theoretical: | 64.96 | 5.77 | 8.91 |
| Found: | 65.34 | 5.76 | 8.82 |

EXAMPLE 22

4-(2,3-Dihydro-1H-inden-2-ylmethyl)-4,5-dihydro-1H-imidazole hemi-fumarate

The procedure is as in Example 16, starting from ethyl (1H-inden-2-yl)acetate.

Melting point: 208–210° C.
Elemental Microanalysis

|  | C % | H % | N % |
| --- | --- | --- | --- |
| Theoretical: | 69.75 | 7.04 | 10.85 |
| Found: | 69.79 | 6.69 | 10.73 |

EXAMPLE 23

4-(Benzo[b]furan-2-ylmethyl)-4,5-dihydro-1H-imidazole fumarate

Step 1: 2-(Bromomethyl)benzo[b]furan 36.40 g (139 mmol) of triphenylphosphine are added, all at once and with vigorous stirring, to a solution, cooled to 0° C., of 10.40 g (70 mmol) of 2-hydroxymethyl-benzo[b]furan and 46 g (139 mol) of CBr$_4$ in 220 ml of ether. After stirring for 4 hours at 20° C., the precipitate formed is suctioned off and washed with Et$_2$O; the filtrate is dried and concentrated, and the residue is then chromatographed on silica, eluting with a mixture of cyclohexane/CH$_2$Cl$_2$=80/20, to yield the expected compound in the form of an oil.

Elemental Microanalysis

|  | C % | H % | N % |
|---|---|---|---|
| Theoretical: | 51.22 | 3.34 | 37.86 |
| Found: | 50.98 | 3.25 | 38.02 |

Step 2: 2-Amino-3-benzo[b]furan-2-ylpropanenitrile 4.40 g (22 mmol) of the compound obtained in Step 1 are added, dropwise and under nitrogen, to a solution, cooled to 0° C., containing 4 g (18 mmol) of N-(diphenyl-methylene) aminoacetonitrile and 0.53 g (1.6 mmol) of tetrabutylammonium bromide in a mixture of 55 ml of toluene and 4.40 g of NaOH 40%. After stirring overnight at 20° C., the mixture is diluted with water and extracted with $CH_2Cl_2$ (3×80 ml); the combined organic phases are washed with $H_2O$ and then with saturated NaCl solution and concentrated in vacuo. The residue is taken up in 100 ml of ether and, with vigorous stirring, treated with 100 ml of 1N HCl. The mixture is stirred for 12 hours at 20° C. and then separated; the aqueous phase is rendered alkaline with 6N NaOH and then extracted with $CH_2Cl_2$ (3×50 ml), and the organic phases are washed with saturated NaCl solution, dried and concentrated. The title compound is obtained in the form of a brown oil, which is used for the following reaction without being otherwise purified.

Step 3: 3-Benzo[b]furan-2-yl-1,2-propanediamine

The procedure is as in Step 2 of Example 14, starting from the nitrile obtained in Step 2.

Elemental Microanalysis

|  | C % | H % | N % |
|---|---|---|---|
| Theoretical: | 69.45 | 7.42 | 14.72 |
| Found: | 69.61 | 7.43 | 14.34 |

Step 4: 4-(Benzo[b]furan-2-ylmethyl)-4,5-dihydro-1H-imidazole fumarate

The procedure is as in Step 5 of Example 1, starting from the diamine obtained in Step 3.

Melting point: 154–156° C.

Elemental Microanalysis

|  | C % | H % | N % |
|---|---|---|---|
| Theoretical: | 60.76 | 5.10 | 8.86 |
| Found: | 60.54 | 5.19 | 8.82 |

Examples 24 and 25 are obtained by proceeding as in Example 23:

EXAMPLE 24

4-[(5-Chloro-2,3-dihydro-1H-2-indenyl)methyl]-4,5-dihydro-1H-imidazole hemi-fumarate Elemental Microanalysis

|  | C % | H % | N % |
|---|---|---|---|
| Theoretical: | 65.20 | 6.20 | 10.14 |
| Found: | 64.82 | 6.20 | 9.90 |

EXAMPLE 25

4-(2-Naphthylmethyl)-4,5-dihydro-1H-imidazole fumarate

Melting point: 149–150° C.

Elemental Microanalysis

|  | C % | H % | N % |
|---|---|---|---|
| Theoretical: | 66.25 | 5.56 | 8.58 |
| Found: | 65.97 | 5.65 | 8.44 |

EXAMPLE 26

4-[1a,2,3,7b-Tetrahydro-1H-cyclopropa[a]naphth-1-ylmethyl]-4,5-dihydro-1H-imidazole fumarate Step 1: Ethyl 1-(1a,2,3,7b-tetrahydro-1H-cyclopropa[a]naphth-1-yl)-acetate 200 ml (20 mmol) of a solution of diethylzinc in hexane (1M) and a solution of 71 g (400 mmol) of chloroiodomethane in 125 ml of 1,2-dichloroethane are added, in succession and dropwise, to a solution, cooled to −25° C., of 7.20 g (33 mmol) of the compound obtained in Example 1 (Step 1) in 75 ml of 1,2-dichloroethane. The temperature of the mixture is increased to 10° C. and stirring is maintained at that temperature for 4 hours. After cooling to 0° C., the mixture is treated with 50 ml of saturated $NH_4Cl$ and then with 100 ml of water, and extracted with $Et_2O$ (3×200 ml). The combined organic phases are washed with saturated NaCl solution, dried and concentrated in vacuo to yield the title compound in the form of an oil.

Elemental Microanalysis

|  | C % | H % |
|---|---|---|
| Theoretical: | 78.23 | 7.88 |
| Found: | 78.53 | 7.64 |

Step 2: 2-(1a,2,3,7b-Tetrahydro-1H-cyclopropa[a] naphth-1-yl)-acetaldehyde

The procedure is as in Step 2 of Example 1, starting from the compound obtained in Step 1.

Elemental Microanalysis

| | C % | H % |
|---|---|---|
| Theoretical: | 83.83 | 7.58 |
| Found: | 83.72 | 7.63 |

Step 3: 4-[1a,2,3,7b-Tetrahydro-1H-cyclopropa[a]
naphth-1-ylmethyl]-4,5-dihydro-1H-imidazole
fumarate The procedure is as in Steps 1,2 and 3 of Example 14, starting from the aldehyde obtained in Step 2. After reaction with formamidine acetate, the compound obtained in Example 26 is composed of a mixture of diastereoisomers (50/50), which are separated by chromatography on silica, eluting with a mixture of $CH_2Cl_2/CH_3OH/NH_4OH=95/5/0.5$. Each isolated diastereoisomer is converted into a salt in conventional manner using fumaric acid and recrystallised from a mixture of acetone/iPrOH.

EXAMPLE 27

(4R)-4-[(1aR,7bR)-1a,2,3,7b-Tetrahydro-1H-
cyclopropa[a]-naphth-1-ylmethyl]-4,5-dihydro-1H-
imidazole fumarate and (4S)-4-[(1aS, 7bS)-1a,2,3,7b-tetrahydro-1H-
cyclopropa[a]-naphth-1-ylmethyl]-4,5-dihydro-1H-
imidazole fumarate Melting point: 192° C.
Elemental Microanalysis

| | C % | H % | N % |
|---|---|---|---|
| Theoretical: | 66.65 | 6.48 | 8.18 |
| Found: | 66.50 | 6.52 | 8.08 |

EXAMPLE 28

(4S)-4-[(1aR,7bR)-1a,2,3,7b-Tetrahydro-1H-
cyclopropa[a]-naphth-1-ylmethyl]-4,5-dihydro-1H-
imidazole fumarate and (4R)-4-[(1aS, 7bS)-1a,2,3,7b-tetrahydro-1H-
cyclopropa[a]-naphth-1-ylmethyl]-4,5-dihydro-1H-
imidazole fumarate Melting point: 204° C.
Elemental Microanalysis

| | C % | H % | N % |
|---|---|---|---|
| Theoretical: | 70.61 | 6.96 | 9.47 |
| Found: | 70.74 | 7.01 | 9.47 |

EXAMPLE 29

4-{Spiro[cyclopropan-2:2'-(1',2',3',4'-tetrahydro-
naphth)]-1-yl}-4,5-dihydro-1H-imidazole fumarate
(isomer 1)

Step 1: Diethyl (1-oxo-1,2,3,4-tetrahydro-2-
naphthyl)phosphonate

A solution of α-tetralone (10 g, 68 mmol) in anhydrous THF (120 ml) is added dropwise to 1M lithium diisopropylamide solution (75 .mol, 75 ml) stirred at −65° C. under nitrogen. After stirring for 45 minutes, diethyl chlorophosphate (12.90 g, 75 mmol) is added to the enolate formed and the temperature of the mixture is progressively raised to 0° C. over a period of 50 minutes. After cooling to −70° C., the mixture is transferred to 2M lithium diisopropylamide solution (150 mmol, 75 ml). The solution obtained is stirred for 2 hours at 10° C. and then treated with acetic acid (272 mmol, 15.5 ml) in ether (250 ml). The mixture is filtered and the filtrate is concentrated. The title compound is obtained by purification on a flash column (eluant: cyclohexane/EtOAc=60/40).

Step 2: 2'-(Tetrahydropyran-2-yloxymethyl)-spiro
[1'-2]cyclopropan-3,4-dihydro-1-oxo-naphthalene A solution of the compound obtained in Step 1 (27 g, 95 mmol) in toluene (60 ml) is added to a suspension of NaH (4.40 g, 109.2 mmol) in toluene (160 ml) at 20° C. under nitrogen. The mixture is stirred at ambient temperature for 1 hour and then 30 g (190 mmol) of 2-oxiranylmethoxy-tetrahydropyran are added. The reaction is heated at reflux for 4 days and the mixture is then cooled, hydrolysed with water and extracted with ether. The organic phase is washed with NaCl solution, dried over $MgSO_4$ and concentrated in vacuo. The residue obtained is chromatographed on a flash column (eluant: cyclohexane/EtOAc=80/20), allowing the title compound to be isolated in the form of a pale red oil.

Elemental Microanalysis

| | C % | H % |
|---|---|---|
| Theoretical: | 75.50 | 7.74 |
| Found: | 75.43 | 7.82 |

Step 3: {Spiro[cyclopropan-2:2'-(1',2',3',4'-
tetrahydronaphth)]-1-yl}-methanol

Solid zinc iodide (4.16 g, 13 mmol) and sodium cyanoborohydride (4.10 g, 62.2 mmol) are added to a solution of the compound obtained in Step 2 (2.50 g, 8.7 mmol) in 1,2-dichloro-ethane (45 ml) at ambient temperature under nitrogen. The reaction mixture is heated at 80–85° C. for 3 hours and then cooled and poured onto ice-cold saturated $NH_4Cl$ solution containing 10%, by volume, 5N HCl (180 ml). The mixture is extracted 3 times with AcOEt and the organic phases are dried over $MgSO_4$ and evaporated. The title alcohol is purified by chromatography on a flash column (eluant: cyclohexane/EtOAc=70/30) and isolated in the form of a colourless oil.

Step 4: {Spiro[cyclopropan-2:2'-(1',2',3',4'-
tetrahydronaphth)]-1-yl}-carboxaldehyde 11.6 g (116.2 mmol) of $CrO_3$ are added to a solution of pyridine (226.5 mmol, 18.5 ml) in $CH_2Cl_2$ (360 ml) at 0° C. under nitrogen. After stirring for 1 hour at ambient temperature, the alcohol obtained in Step 3 (3.64 g, 19.4 mmol), dissolved in $CH_2Cl_2$ (80 ml), is added; the mixture is stirred for a further 2 hours at ambient temperature and then filtered, and the filtrate is evaporated under reduced pressure. The residue is diluted with ether, washed with 1N NaOH, 1N HCl and saturated NaCl solution, then dried over $MgSO_4$ and evaporated under reduced pressure to yield the title aldehyde in the form of an oil.

Step 5: {Spiro[cyclopropan-2:2'-(1',2',3',4'-
tetrahydronaphth)]-1-yl}-aminoacetonitrile 760 mg (14.2 mmol) of KCN and 920 mg (14.2 mmol) of $NH_4Cl$ are added, in succession, to a solution, vigorously stirred under nitrogen, containing 2.63 g (14.1 mmol) of the compound obtained in Step 4, 430 ml of MeOH and 20 ml of water. After stirring for 12 hours at 20° C., the solution is diluted with $CH_2Cl_2$ and extracted 3 times with $CH_2Cl_2$. The organic phase is washed with saturated NaCl solution, dried over $MgSO_4$ and concentrated. The residue obtained is treated with 30 ml of 7N methanolic ammonia solution and stirred in a closed system for 12 hours at 20° C. After evaporation under reduced pressure, the title compound is obtained in the form of a brown oil.

Step 6: 1-{Spiro[cyclopropan-2:2'-(1',2',3',4'-tetrahydronaphth)-1-yl}-ethane-1,2-diamine A solution of the compound obtained in Step 5 (2.90 g, 13.7 mmol) in anhydrous THF (60 ml) is added dropwise to a suspension of $LiAlH_4$ (570 mg, 15 mmol) in 60 ml of THF at −20° C. under nitrogen. The mixture is stirred for 2 hours at −10° C. and then hydrolysed by successive additions of $H_2O$ (3.5 ml), NaOH 35% (7 ml) and $H_2O$ (7.3 ml). The suspension obtained is filtered and the filtrate is evaporated. The oil obtained is purified by chromatography on a flash column and yields a mixture of 2 diastereoisomers, which are separated by HPLC (Kromasil 100,5 C18-265mm-$CH_3OH/H_2O/CF_3COOH$:350/650/5).

Step 7: 4-{Spiro[cyclopropan-2:2'-(1',2',3+,4'-tetrahydro-naphth)]-1-yl}-4,5-dihydro-1H-imidazole fumarate (isomer 1)

A mixture containing one of the two diastereoisomers obtained in Step 6 (170 mg, 0.8 mmol) and formamidine acetate (94 mg, 0.9 mmol) in ethanol (5 ml) is stirred at 20° C. under nitrogen for 12 hours. The solvent is then evaporated off and the residue is taken up in 1N HCl. The acidic phase is washed with $Et_2O$ and rendered basic with sodium hydroxide solution. The mixture is extracted with $CH_2Cl_2$ and the organic phase is washed, dried over $MgSO_4$ and evaporated. The solid residue obtained is dissolved in acetone (10 ml) and treated with a solution of fumaric acid (81.5 mg, 0.7 mmol) in isopropanol (4 ml). After evaporation and recrystallisation from a mixture of acetone/isopropanol, the title compound is obtained in the form of a white powder.

Melting point: 149° C.

EXAMPLE 30

4-{Spiro[cyclopropan-2:2'-(1',2',3',4'-tetrahydro-naphth)]-1-yl}-4,5-dihydro-1H-imidazole fumarate (isomer 2)

The procedure is as in Step 7 of Example 29, starting from the other diastereoisomer isolated in Step 6 of Example 29.

Melting point: 164° C.
Elemental Microanalysis

|  | C % | H % | N % |
|---|---|---|---|
| Theoretical: | 66.65 | 6.48 | 8.18 |
| Found: | 66.59 | 6.65 | 8.22 |

EXAMPLE 31

4-[(8-Chloro-1,2,3,4-tetrahydro-2-naphthyl)methyl]-4,5-dihydro-1-imidazole fumarate The procedure is as in Example 16, starting from ethyl 2-(8-chloro-3,4-dihydro-2-naphthyl)acetate.

Melting point: 230–233° C.
Elemental Microanalysis

|  | C % | H % | N % | % Cl |
|---|---|---|---|---|
| Theoretical: | 59.26 | 5.80 | 7.68 | 9.72 |
| Found: | 59.44 | 5.95 | 7.64 | 9.93 |

EXAMPLE 32

4-[(5-Fluoro-2,3-dihydro-1H-inden-2-yl)methyl]-4,5-dihydro-1H-imidazole hemi-fumarate The procedure is as in Example 23, starting from 2-hydroxymethyl-5-fluoroindan.

Melting point: 187–190° C.
Elemental Microanalysis

|  | C % | H % | N % |
|---|---|---|---|
| Theoretical: | 65.20 | 6.20 | 10.14 |
| Found: | 64.82 | 6.20 | 9.90 |

EXAMPLE 33

4-[(4-Fluoro-2,3-dihydro-1H-inden-2-yl)methyl]-4,5-dihydro-1H-imidazole hemi-fumarate The procedure is as in Example 23, starting from 2-hydroxymethyl-4-fluoroindan.

Melting point: 212–215° C.
Elemental Microanalysis

|  | C % | H % | N % |
|---|---|---|---|
| Theoretical: | 65.20 | 6.20 | 10.14 |
| Found: | 64.34 | 6.32 | 9.89 |

EXAMPLE 34

4-[(5,6-Difluoro-2,3-dihydro-1H-inden-2-yl)methyl]-4,5-dihydro-1H-imidazole hemi-fumarate The procedure is as in Example 23, starting from 2-hydroxymethyl-5,6-difluoroindan.

Melting point: 201–202° C.
Elemental Microanalysis

|  | C % | H % | N % |
|---|---|---|---|
| Theoretical: | 61.22 | 5.48 | 9.52 |
| Found: | 61.04 | 5.54 | 9.47 |

EXAMPLE 35

4[(5,6-Dimethyl-2,3-dihydro-1H-inden-2-yl)methyl]-4,5-dihydro-1H-imidazole fumarate The procedure is as in Example 23, starting from 2-hydroxymethyl-5,6-dimethylindan.

Melting point: 198–200° C.

Elemental Microanalysis

|  | C % | H % | N % |
|---|---|---|---|
| Theoretical: | 66.26 | 7.02 | 8.13 |
| Found: | 66.37 | 7.07 | 8.09 |

EXAMPLE 36

4-[(5-Fluoro-1-benzofuran-2-yl)methyl]-4,5-dihydro-1H-imidazole fumarate

The procedure is as in Example 23, starting from 2-hydroxymethyl-5-fluorobenzo[b]furan.

Melting-point: 148–151° C.

Elemental Microanalysis

|  | C % | H % | N % |
|---|---|---|---|
| Theoretical: | 57.49 | 4.52 | 8.38 |
| Found: | 57.51 | 4.68 | 8.27 |

EXAMPLE 37

4-(3,4-Dihydro-2-naphthylmethyl)-1-methyl-4,5-dihydro-1H-imidazole 1,5 fumarate 0.205 ml (1.5 mmol) of triethylamine and then 0.165 ml (1.75 mmol) of dimethyl sulphate are added, in succession, to a solution of 320 mg (1.5 mmol) of the compound obtained in Example 1 (after neutralisation of the salt by 2N NaOH) in 10 ml of $CH_2Cl_2$, cooled to −60° C. The temperature is then increased to 20° C. and the mixture is stirred at that temperature for 12 hours. The mixture is washed with 0.1N NaOH (5 ml) and then with saturated NaCl solution. After drying and evaporating off the solvent, the residue is chromatographed on silica, eluting with a mixture of $CH_2Cl_2/CH_3OH/NEt_3=90/10/0.5$. The initial fraction is dissolved in 5 ml of EtOH and then treated with a solution of 71 mg (0.61 mmol) of fumaric acid in 5 ml of EtOH. After concentration, the title compound is isolated by recrystallisation.

Melting point: 190–192° C.

Elemental Microanalysis

|  | C % | H % | N % |
|---|---|---|---|
| Theoretical: | 62.99 | 6.05 | 7.00 |
| Found: | 63.22 | 6.10 | 6.97 |

EXAMPLE 38

4-[(7-Fluoro-1,2,3,4-tetrahydro-2-naphthyl)methyl]-4,5-dihydro-1H-imidazole fumarate (diastereoisomer 1)

Step 1: N-{2-(1-Cyclohexen-1-ylamino)-1-[(7-fluoro-3,4-dihydro-2-naphthyl)methyl]-2-oxoethyl}-N-[(1R)-1-phenylethyl]benzamide A solution of 15 g (78 mmol) of 7-fluoro-3,4-dihydro-2-naphthalenecarboxaldehyde (obtained according to the same procedure as in Steps 1 and 2 of Example 1, starting from 7-fluoro-1,2,3,4-tetrahydronaphthalen-2-one) and 9.45 g (78 mmol) of (1R)-1-phenylethyl-amine in 150 ml of methanol is stirred at 20° C. under a nitrogen atmosphere for 1 hour. 9.76 g (80 mmol) of benzoic acid and 8.56 g (80 mmol) of 1-cyclohexenyl-isonitrile are then added in succession; the mixture is then stirred at 20° C. for 15 hours. After concentration in vacuo, the residue is taken up in EtOAc (300 ml); the solution is washed with 0.1N aq. NaOH, then with 0.1N aq. HCl and finally with saturated aq. NaCl. The organic phase is concentrated in vacuo; chromatography of the oily residue, eluting with a mixture of cyclohexane/EtOAc=80/20, allows 2 diastereoisomers (1 and 2) of the title compound to be isolated in the form of oils.

Rf(1)=0.25 Rf(2)=0.15

Step 2: N-{2-Amino-1-[(7-fluoro-3,4-dihydro-2-naphthyl)methyl]-2-oxoethyl}-N-[(1R)-1-phenylethyl]benzamide A solution of 3.50 g (6.70 mmol) of diastereoisomer 2 from Step 1 in 50 ml of THF is treated with 1.20 ml of concentrated HCl. After stirring for 1 hour at 20° C., the mixture is neutralised by adding solid $NaHCO_3$, filtered and concentrated in vacuo. Chromatography on $SiO_2$, eluting with a mixture of cyclohexane/EtOAc=40/60, allows the title compound to be obtained in the form of a foam.

Elemental Microanalysis

|  | C % | H % | N % |
|---|---|---|---|
| Theoretical: | 76.00 | 6.15 | 6.33 |
| Found: | 76.20 | 6.30 | 5.95 |

Step 3: N-{2-Amino-1-[(7-fluoro-1,2,3,4-tetrahydro-2-naphthyl)methyl]-2-oxoethyl}-N-[(1R)-1-phenylethyl]benzamide A suspension of 2.70 g (6.10 mmol) of the compound obtained in Step 2 and 1 g of $Pd(OH)_2$ in 120 ml of EtOH is hydrogenated under one atmosphere for 12 hours. After filtering off the catalyst, the solvent is evaporated off in vacuo. The residue obtained is chromatographed on $SiO_2$, eluting with a solution of cyclohexane/EtOAc=40/60, to yield the title compound in the form of 2 diastereoisomers.

Diastereoisomer 1:

Melting point: 145–146° C.

Elemental Microanalysis

|  | C % | H % | N % |
|---|---|---|---|
| Theoretical: | 75.65 | 6.58 | 6.30 |
| Found: | 75.46 | 6.62 | 6.48 |

Step 4: N-{2-Amino-1-[(7-fluoro-1,2,3,4-tetrahydro-2-naphthyl)methyl]-ethyl}-N-benzyl-N-[(1R)-1-phenylethyl]amine 7 ml (7 mmol) of a molar solution of $BH_3$/THF are added, dropwise and with vigorous stirring, to a solution, maintained under nitrogen, of 1.20 g (2.70 mmol) of the compound obtained in Step 3 (diastereoisomer 1) in 30 ml of anhydrous THF. The mixture is then heated at 70° C. for 1 hour and is then cooled, treated with 8 ml of $CH_3OH$ and stirred at 20° C. for 1 hour. After concentrating in vacuo, the residue is chromatographed on silica, eluting with a solution of $CH_2Cl_2/CH_3OH=95/5$, to yield the title compound in the form of an oil.

Step 5: 3-(7-Fluoro-1,2,3,4-tetrahydro-2-naphthyl)-1,2-propanediamine 0.45 g of ammonium formate is added to a vigorously stirred suspension of 0.35 g (0.84 mmol) of the compound obtained in Step 4 and 0.25 g of Pd/C 10% in 25 ml of $CH_3OH$. After stirring for 1 hour under reflux, the mixture is cooled and filtered; the catalyst is washed with $CH_3OH$ and the combined filtrates are concentrated in vacuo to yield the title compound in the form of an oil, which is used without purification in the following reaction.

Step 6: 4-[(7-Fluoro-1,2,3,4-tetrahydro-2-naphthyl) methyl]-4,5-dihydro-1H-imidazole fumarate (diastereoisomer 1)

The procedure is as in Step 5 of Example 1, starting from the compound obtained in Step 5 hereinabove.

Melting point: 174–175° C.
Elemental Microanalysis

|  | C % | H % | N % |
|---|---|---|---|
| Theoretical: | 62.06 | 6.08 | 8.04 |
| Found: | 62.25 | 6.39 | 8.08 |

EXAMPLE 39

4[-(7-Fluoro-1,2,3,4-tetrahydro-2-naphthyl)methyl]-4,5-dihydro-1H-imidazole fumarate (diastereoisomer 2)

The procedure is as in Example 38, taking the diastereoisomer 2 obtained in Step 3.

| Diastereoisomer 2: Foam Elemental microanalysis: | | | |
|---|---|---|---|
|  | C % | H % | N % |
| Theoretical: | 75.65 | 6.58 | 6.30 |
| Found: | 75.38 | 6.66 | 6.40 |

Melting point: 170–172° C.

EXAMPLE 40

4-[(7-Fluoro-1,2,3,4-tetrahydro-2-naphthyl)methyl]-4,5-dihydro-1H-imidazole fumarate (mixture of diastereoisomers 3 and 4)

The procedure is as in Example 38, taking the diastereoisomer 1 obtained in Step 1.

Melting point: 170–171° C.
Elemental Microanalysis

|  | C % | H % | N % |
|---|---|---|---|
| Theoretical: | 62.06 | 6.08 | 8.04 |
| Found: | 62.31 | 6.14 | 8.07 |

EXAMPLE 41

4-[(8-Chloro-2-naphthyl)methyl]-4,5-dihydro-1H-imidazole fumarate

The procedure is as in Steps 2, 3 and 4 of Example 23, starting from 2-bromomethyl-8-chloronaphthalene.

Melting point: 172–175° C.
Elemental Microanalysis

|  | C % | H % | N % | Cl % |
|---|---|---|---|---|
| Theoretical: | 59.92 | 4.75 | 7.76 | 9.83 |
| Found: | 59.55 | 4.79 | 7.58 | 10.00 |

EXAMPLE 42

4-[(7-Fluoro-2-naphthyl)methyl]-4,5-dihydro-1H-imidazole fumarate

The procedure is as in Steps 2, 3 and 4 of Example 23, starting from 2-bromomethyl-7-fluoronaphthalene.

Melting point: 157–160° C.
Elemental Microanalysis

|  | C % | H % | N % |
|---|---|---|---|
| Theoretical: | 62.79 | 4.98 | 8.14 |
| Found: | 62.41 | 5.08 | 8.11 |

EXAMPLE 43

4-Methyl-4-(1,2,3,4-tetrahydro-2-naphthylmethyl)-4,5-dihydro-1H-imidazole fumarate (diastereoisomer 1)

Step 1: 3-(3,4-Dihydro-2-naphthyl)-2-methyl-2-[(1-phenylethyl)amino]propanenitrile A solution of 9.50 g (51 mmol) of (3,4-dihydro-naphth-2-yl)-propan-2-one, 6.17 g (51 mmol) of R-α-methyl-benzylamine and 0.095 g (0.5 mmol) of p-toluenesulphonic acid in 250 ml of toluene is heated at reflux with azeotropic distillation of the water/toluene mixture for 8 hours. After cooling and evaporating off the solvent, the residue is dissolved in 450 ml of $CH_2Cl_2$; 5.50 g (55 mmol) of trimethylsilyl cyanide are added, in portions, to the resulting mixture, cooled to −35° C., under a nitrogen atmosphere. After stirring for 10 hours at −35° C., the mixture is concentrated in vacuo to yield the title compound, in the form of an oil, which is used without purification for the following reaction.

Step 2: N-[2-Amino-1-(3,4-dihydro-2-naphthylmethyl)-1-methylethyl]-N-(1-phenyl-ethyl)amine A solution of 16 g of the compound obtained in Step 1 in 200 ml of THF is added dropwise to a suspension, maintained under nitrogen, of 2.28 g (60 mmol) of LiAlH4 in 200 ml of THF. The temperature of the mixture is then increased to 20° C. and stirring is maintained at that temperature for 3 hours. The mixture is again cooled to 0° C. and hydrolysed by successive additions of 20 ml of iPrOH and 25 ml of saturated NaCl solution. The precipitate formed is suctioned off and rinsed with THF; the filtrate is concentrated in vacuo and the residue is chromatographed on silica, eluting with a mixture of $CH_2Cl_2/CH_3OH/NH_4OH=97/3/0.3$, to yield the title compound in the form of 2 diastereoisomers:

diastereoisomer 1: oil–Rf=0.18
diastereoisomer 2: oil–Rf=0.15

Step 3: N-[2-Amino-1-methyl-1-(1,2,3,4-tetrahydro-2-naphthylmethyl)ethyl]-N-(1-phenylethyl)amine A suspension of 0.52 g (1.62 mmol) of the compound obtained in Step 2 (diastereoisomer 1) and of 0.1 g of Pd/Al$_2$O$_3$ in 60 ml of EtOH is hydrogenated at 20° C. under 1 bar for 16 hours. The mixture is then filtered and concentrated in vacuo to yield the title compound in the form of a foam.

Step 4: 2-Methyl-3-(1,2,3,4-tetrahydro-2-naphthyl)-1,2-propanediamine

A suspension of 0.50 g (1.55 mmol) of the compound obtained in Step 3 and 0.14 g of Pd(OH)$_2$ in a mixture of 0.8 ml of acetic acid and 50 ml of EtOH is hydrogenated at 20° C. under 1 bar for 20 hours. After filtration of the mixture and concentration in vacuo, the residue is taken up in 1N aq. NaOH (10 ml) and extracted with CH$_2$Cl$_2$ (3×10 ml); the combined organic phases are washed with saturated aq. NaCl, dried and concentrated to yield the title compound in the form of an oil, which is used in the following reaction without being otherwise purified.

Step 5: 4-Methyl-4-(1,2,3,4-tetrahydro-2-naphthylmethyl)-4,5-dihydro-1H-imidazole fumarate (diastereoisomer 1)

The procedure is as in Step 5 of Example 1, starting from the compound obtained in Step 4.
Melting point: 118° C.
Elemental Microanalysis:

|  | C % | H % | N % |
| --- | --- | --- | --- |
| Theoretical: | 66.26 | 7.02 | 8.13 |
| Found: | 65.98 | 7.01 | 8.22 |

EXAMPLE 44

4-Methyl-4-(1,2,3,4-tetrahydro-2-naphthylmethyl)-4,5-dihydro-1H-imidazole fumarate (diastereoisomer 2)

The procedure is as in Example 43 taking, in Step 3, the diastereoisomer 2 obtained in Step 2.
Melting point: 121° C.
Elemental Microanalysis

|  | C % | H % | N % |
| --- | --- | --- | --- |
| Theoretical: | 66.26 | 7.02 | 8.13 |
| Found: | 66.11 | 7.11 | 8.16 |

EXAMPLE 45

4-{Spiro[cyclopropan-2':2"-(5",6"-difluoro-indan)]-1'-yl}4,5-dihydro-1H-imidazole fumarate (diastereoisomer 1)

Step 1: {Spiro[cyclopropan-2:2'-(5',6'-difluoro-1'-indanone)]-1-yl}-carboxylic acid ethyl ester NaH (3.43 g, 140 mmol) is added, in portions, to a solution of 5,6-difluoro-1-indanone (20 g, 120 mmol) and ethyl 2-[(diethoxy-phosphoryl)oxy]acrylate (36 g, 140 mmol) in THF (260 ml) in such a manner that the temperature does not exceed 35° C. At the end of the addition, the flask is immersed in an oil bath at 50° C. and the temperature of the reaction increases to 60° C. When the temperature returns to 45° C., stirring is carried out for one hour at that temperature. The reaction mixture is poured onto a mixture of ice (1 liter) and 1N hydrochloric acid (1 liter) and the product is extracted with ethyl acetate (3×600 ml); the organic solution is dried over MgSO$_4$ and evaporated. The title compound is purified by chromatography on silica gel (eluant: cyclohexane/ethyl acetate 93/7).

Step 2: {Spiro[cyclopropan-2:2'-(5',6'-difluoro-indan)]-1-yl}-carboxylic acid ethyl ester The product obtained in Step 1 (24.2 g, 90 mmol) is introduced into a 1-liter flask provided with a mechanical stirrer and containing 500 ml of 1,2-dichloroethane, NaBH$_3$CN (42.7 g, 680 mmol) and ZnI$_2$ (41.5 g, 130 mmol). The suspension is heated at reflux, with stirring, for 14 hours. The salts are then filtered off; the solution is hydrolysed with a mixture of NH$_4$Cl 10% (1 liter) and 6N HCl (180 ml), the organic phase is separated off after half an hour and the aqueous phase is extracted with ethyl acetate (2×500 ml). The salts are hydrolysed in the same aqueous phase, which is again extracted with ethyl acetate (2×300 ml). The combined organic phases are washed with Na$_2$CO$_3$ (500 ml) and NaCl (500 ml), dried over MgSO$_4$ and concentrated in vacuo. The title compound is purified by chromatography on silica gel (eluant: cyclohexane/ethyl acetate 95/5).

Step 3: {Spiro[cyclopropan-2:2'-(5',6'-difluoro-indan)]-1-yl}-carbinol

The product obtained in Step 2 (13.9 g, 53 mmol) dissolved in THF (250 ml) is added dropwise to a suspension of LiAlH4 (3.1 g, 82 mmol) in THF (250 ml) at −18° C. The mixture is stirred for 3 hours at ambient temperature and decomposed by the successive addition of water (3.1 ml), 1N NaOH (3.1 ml) and water (6.2 ml). The suspension is stirred overnight, the solid is filtered off and the filtrate is evaporated to yield the title compound, which is used in the following Step without additional purification.

Step 4: {Spiro[cyclopropan-2:2'-(5',6'-difluoro-indan)]-1-yl}-carboxaldehyde

The product obtained in Step 3 (14.3 g, 68 mmol) dissolved in 140 ml of CH$_2$Cl$_2$ is added, dropwise and at ambient temperature, to a suspension of pyridinium chromate prepared at 0° C., starting from pyridine (68 ml, 670 mmol) and CrO$_3$ (42 g, 420 mmol) in 1 liter of CH$_2$Cl$_2$. The suspension is stirred for 5 hours, filtered and the precipitate is washed with ether; the filtrates are evaporated to dryness, taken up in ether (1 liter) and the insoluble material is filtered off. The organic phase is washed, in succession, with 1N NaOH (1 liter), 1N HCl (2×750 ml), NaHCO$_3$ 10% (2×500 ml) and NaCl (500 ml), dried over MgSO$_4$ and evaporated to yield the title compound which is used in the following Step without an additional purification step.

Step 5: 2-Di(4-methoxyphenyl)-methylamino-2-{spiro[cyclopropan-2':2"-(5",6"-difluoro-indan)]-1'-yl}-acetonitrile The product obtained in Step 4 (12 g, 58 mmol) is stirred in 250 ml of CH$_2$Cl$_2$ for 2 hours in the presence of di(4-methoxyphenyl)methylamine (14 g, 58 mmol) and 4 Å molecular sieve (18 g). 6.3 g of (CH$_3$)$_3$SiCN (64 mmol) are then added and the solution is stirred at ambient temperature for 14 hours. The solid is filtered off, the organic phase is washed with 0.1N NaOH (500 ml) and NaCl (250 ml), dried over MgSO$_4$ and evaporated to yield the title compound, which is used in the following Step without additional purification.

Step 6: 2-Di(4-methoxyphenyl)-methylamino-2-{spiro[cyclopropan-2':2"-(5",6"-difluoro-indan)]-1'-yl}-ethylamine (diastereoisomer 1)

The product obtained in Step 5 (26.7 g, 68 mmol), dissolved in THF (125 ml), is added, dropwise and at −10°

C., to a suspension of LiAlH4 (3.3 g, 87 mmol) in THF (500 ml). At the end of the addition, the temperature increases and the suspension is stirred for 1 hour before being decomposed by the successive addition of water (3.3 ml), 1N NaOH (3.3 ml) and water (6.6 ml). After adding ether (300 ml), the suspension is stirred for 45 minutes, the solid is filtered off and the filtrate is evaporated. The diastereoisomers are separated by chromatography on silica gel, eluting with a gradient of ammonia (10% in absolute ethanol) in $CH_2Cl_2$.

Step 7: 2-Amino-2-{spiro[cyclopropan-2':2"-(5",6"-difluoro-indan)]-1'-yl}-ethylamine (diastereoisomer 1)

The product obtained in Step 6 (diastereoisomer 1) (3.12 g, 6.7 mmol) is dissolved in a mixture of $AcOH/H_2O$ (80/20, 200 ml) and the solution is immersed in an oil bath at 90° C. for 45 minutes. The acetic acid is then evaporated off. The syrup obtained is dissolved in 1N HCl (100 ml) and the solution is washed with ether (3×75 ml). The aqueous phase is neutralised with NaOH 35% (20 ml), extracted with $CH_2Cl_2$ (3×75 ml), dried over $K_2CO_3$ and evaporated. The title compound is purified by chromatography on silica gel (eluant: $CH_2Cl_2/MeOH/NH_4OH$ 90/9/1).

Step 8: 4-{Spiro[cyclopropan-2':2"-(5",6"-difluoro-indan)]-1'-yl}-4,5-dihydro-1H-imidazole fumarate (diastereoisomer 1)

Formamidine acetate (654 mg, 6.3 mmol) is added to a solution of the compound obtained in Step 7 (1.5 g, 6.3 mmol) in EtOH (100 ml). After stirring for 14 hours at ambient temperature, the ethanol is evaporated off and the white solid is taken up in acetone (75 ml) and isopropanol (10 ml). The solution is filtered and fumaric acid (694 mg, 6.3 mmol), previously dissolved, with warming, in acetone (25 ml) and isopropanol (10 ml), is added. The title compound is obtained in the form of a solid, which is filtered off and dried in vacuo.

Melting point: 220° C. (decomposition)
Elemental Microanalysis

|  | C % | H % | N % |
|---|---|---|---|
| Theoretical: | 59.34 | 4.98 | 7.69 |
| Found: | 59.43 | 5.17 | 7.58 |

EXAMPLE 46

4-{Spiro[cyclopropan-2':2"-(5",6"-difluoro-indan)]-1'-yl}-4,5-dihydro-1H-imidazole fumarate (diastereoisomer 2)

The procedure is as in Steps 7 and 8 of Example 45, starting from the second diastereoisomer isolated in Step 6.
Melting point: 240° C. (decomposition)
Elemental Microanalysis :

|  | C % | H % | N % |
|---|---|---|---|
| Theoretical: | 59.34 | 4.98 | 7.69 |
| Found: | 59.46 | 4.98 | 7.59 |

EXAMPLE 47

4-[Spiro(cyclopropan-2':2"-indan)-1'-yl]-4,5-dihydro-1H-imidazole hemi-fumarate (diastereoisomer 1)

The procedure is as in Steps 1 to 8 of Example 45, starting from 1-indanone.

Melting point: 212° C.
Elemental Microanalysis

|  | C % | H % | N % |
|---|---|---|---|
| Theoretical: | 71.09 | 6.71 | 10.36 |
| Found: | 70.70 | 6.85 | 10.32 |

EXAMPLE 48

4-[Spiro(cyclopropan-2':2"-indan)-1'-yl]-4,5-dihydro-1H-imidazole fumarate (diastereoisomer 2)

The procedure is as in Steps 1 to 8 of Example 46, starting from 1-indanone.
Melting point: 212° C.
Elemental Microanalysis

|  | C % | H % | N % |
|---|---|---|---|
| Theoretical: | 65.84 | 6.14 | 8.53 |
| Found: | 65.86 | 6.40 | 8.66 |

EXAMPLE 49

4-{Spiro[cyclopropan-2':2"-(8"-chloro-1",2",3",4"-tetrahydro-naphth)]-1'-yl}-4,5-dihydro-1H-imidazole fumarate (diastereoisomer 1)

The procedure is as in Steps 1 to 8 of Example 45, starting from 8-chloro-1-tetralone.
Melting point: 175° C.
Elemental Microanalysis

|  | C % | H % | N % |
|---|---|---|---|
| Theoretical: | 60.56 | 5.62 | 7.43 |
| Found: | 60.16 | 5.73 | 7.26 |

EXAMPLE 50

4-{Spiro[cyclopropan-2':2"-(8"-chloro-1",2",3",4"-tetrahydro-naphth)]-1'-yl}-4,5-dihydro-1H-imidazole fumarate (diastereoisomer 2)

The procedure is as in Steps 1 to 8 of Example 46, starting from 8-chloro-1-tetralone.
Melting point: 194° C.
Elemental Microanalysis

|  | C % | H % | N % | Cl % |
|---|---|---|---|---|
| Theoretical: | 60.56 | 5.62 | 7.43 | 9.41 |
| Found: | 60.24 | 5.61 | 7.48 | 9.41 |

EXAMPLE 51

4-{Spiro[cyclopropan-2':2"-(1",2",3",4"-tetrahydro-naphth)]-1"-yl}-4,5-dihydro-1H-imidazole fumarate (enantiomer 1 of the product of Example 30)

The second diastereoisomer from Step 6 of Example 29 is dissolved in ethanol in the presence of one equivalent of R(−) mandelic acid. The solid that crystallises is recrystallised from ethanol. The salt is decomposed by neutralising an aqueous solution with 1N NaOH; the solution is then extracted with dichloromethane, dried over $K_2CO_3$ and evaporated in vacuo. The residue is treated as in Step 7 of Example 29 to yield the title compound.

Melting point: 173.6° C.
Elemental Microanalysis

|  | C % | H % | N % |
|---|---|---|---|
| Theoretical: | 66.65 | 6.48 | 8.18 |
| Found: | 66.35 | 6.48 | 8.14 |

EXAMPLE 52

4-{Spiro[cyclopropan-2':2"-(1",2",3",4"-tetrahydronaphth)]-1'-yl}-4,5-dihydro-1H-imidazole fumarate
(enantiomer 2 of the product of Example 30)

The second diastereoisomer from Step 6 of Example 29 is dissolved in ethanol in the presence of one equivalent of S(+) mandelic acid. The solid that crystallises is recrystallised from ethanol. The salt is decomposed by neutralising an aqueous solution with 1N NaOH; the solution is then extracted with dichloromethane, dried over $K_2CO_3$ and evaporated in vacuo. The residue is treated as in Step 7 of Example 29 to yield the title compound.

Melting point: 172.5° C.
Elemental Microanalysis

|  | C % | H % | N % |
|---|---|---|---|
| Theoretical: | 66.65 | 6.48 | 8.18 |
| Found: | 66.34 | 6.50 | 8.16 |

EXAMPLE 53

4[(2-Methyl-1,2,3,4-tetrahydro-2-naphthyl)methyl]-4,5-dihydro-1H-imidazole fumarate
(diastereoisomer 1)

The procedure is as in steps 5 to 8 of Example 45, starting from (2-methyl-1,2,3,4-tetrahydronaphth-2-yl)acetaldehyde.

Melting point: 154° C.
Elemental Microanalysis

|  | C % | H % | N % |
|---|---|---|---|
| Theoretical: | 66.26 | 7.02 | 8.13 |
| Found: | 65.72 | 7.17 | 8.28 |

EXAMPLE 54

4-[(2-Methyl-1,2,3,4-tetrahydro-2-naphthyl)methyl]-4,5-dihydro-1H-imidazole fumarate
(diastereoisomer 2)

The procedure is as in steps 5 to 8 of Example 45, starting from (2-methyl-1,2,3,4-tetrahydronaphth-2-yl)acetaldehyde.

Melting point: 152° C.
Elemental Microanalysis

|  | C % | H % | N % |
|---|---|---|---|
| Theoretical: | 66.26 | 7.02 | 8.13 |
| Found: | 66.22 | 7.36 | 8.27 |

PHARMACOLOGICAL STUDY

EXAMPLE A

Determination of the Affinity for $\alpha_2$-adrenergic Receptors in the Rat

The affinity was determined by competition experiments with [$^3$H]-RX 821,002. The membranes are prepared from the cerebral cortex of the rat and are incubated in triplicate with 0.4 nM [$^3$H]-RX 821,002 and the compound being tested in a final volume of 1.0 ml, for 60 minutes at 22° C. The incubation buffer contains 50 nM TRIS-HCl (pH 7.5), 1 mM EDTA and 100 µM GppNHp. The non-specific binding is determined using 10 µM phentolamine.

Data Analysis

At the end of the incubation, the incubation medium is filtered through WHATMAN GF/B filters impregnated with 0.1% of polyethylenimine and washed three times with 5 ml of cooled buffer. The radioactivity retained on the filters is determined by liquid scintillation counting. The binding isotherms are analysed by non-linear regression.

Result

The compounds of the invention exhibit a specific $\alpha_2$-adrenergic receptor antagonist activity with the compound of Example 22, for example, having a pKi of 8.8.

EXAMPLE B

Determination of the Affinity for Noradrenaline Reuptake Sites in the Rat

The affinity was determined by competition experiments using [$^3$H]-nisoxetine. The membranes are prepared from the frontal cortex of the rat and are incubated in triplicate with 2 nM [$^3$H]-nisoxetine and the compound being tested in a final volume of 0.5 ml, for 4 hours at 4° C. The incubation buffer contains 50 mM TRIS-HCl (pH 7.4), 120 mM NaCl and 5 mM KCl. The non-specific binding is determined using 10 µM desipramine.

Data Analysis

At the end of the incubation, the incubation medium is filtered through WHATMAN GF/B filters impregnated with 0.1% of polyethylenimine and washed three times with 5 ml of cooled buffer. The radioactivity retained on the filters is determined by liquid scintillation counting. The binding isotherms are analysed by non-linear regression.

Result

The compounds of the present invention exhibit very good affinity for noradrenaline reuptake sites. By way of example, the pKi of the compound of Example 2 is 7.8.

EXAMPLE C

Determination of the Affinity for Serotonin Reuptake Sites in the Rat

The affinity was determined by competition experiments using [$^3$H]-paroxetine. The membranes are prepared from the frontal cortex of the rat and are incubated in triplicate with 0.25 nM [$^3$H]-paroxetine and the compound being tested in a final volume of 0.4 ml, for 2 hours at 25° C. The incubation buffer contains 50 mM TRIS-HCl (pH 7.4), 120 mM NaCl and 5 mM KCN. The non-specific binding is determined using 10 μM citalopram.

Data Analysis

At the end of the incubation, the incubation medium is filtered through WHATMAN GF/B filters impregnated with 0.1% of polyethylenimine and washed three times with 5 ml of cooled buffer. The radioactivity retained on the filters is determined by liquid scintillation counting. The binding isotherms are analysed by non-linear regression.

Result

The compounds of the present invention exhibit very good affinity for serotonin reuptake sites. By way of example, the pKi of the compound of Example 12 is 7.8.

EXAMPLE D

Pharmaceutical Composition: Tablets

| | |
|---|---|
| 1000 tablets each containing 5 mg of 4-[(8-methoxy-3,4-dihydro-2-naphthyl)methyl]-4,5-dihydro-1H-imidazole fumarate (Example 12) | 5 g |
| Wheat starch | 20 g |
| Maize starch | 20 g |
| Lactose | 30 g |
| Magnesium stearate | 2 g |
| Silica | 1 g |
| Hydroxypropyl cellulose | 2 g |

We claim:
1. A compound selected from those of formula (I):

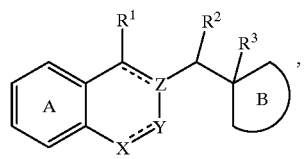

(I)

wherein:

A represents a benzene ring unsubstituted or substituted by from 1 to 4 identical or different groups selected from linear or branched ($C_1$–$C_6$)alkyl, linear or branched ($C_1$–$C_6$)alkoxy, hydroxy, polyhalo-($C_1$–$C_6$)alkyl in which the alkyl moiety is linear or branched, cyano, nitro, amino, alkylamino, dialkylamino, thioalkyl, sulphonylalkyl, sulphinylalkyl, carboxy, alkoxycarbonyl, alkylcarbonyloxy, formyl, carbamoyl, carboxamide, phenyl, benzyl, and halogen, B represents an imidazoline ring as represented in formula (Ia) or (Ib):

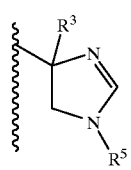

(Ia)

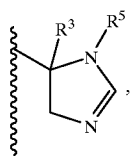

(Ib)

X represents
  $CR^6$ or $CR^6R^7$ (wherein $R^6$ and $R^7$, which may be the same or different, each represent hydrogen or linear or branched ($C_1$–$C_6$)alkyl),
  nitrogen or $NR^8$ (wherein $R^8$ represents hydrogen or linear or branched ($C_1$–$C_6$)alkyl or benzyl),
  oxygen,
  sulphur or SO or $SO_2$, Y represents CH or $CH_2$ or a single bond (and, in that case, the ring containing X, Y and Z is represented by the formula (1c)

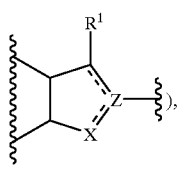

(Ic)

Z represents carbon or $CR^4$ wherein $R^4$ represents hydrogen or linear or branched ($C_1$–$C_6$)alkyl, $R^1$, $R^2$, $R^3$, which may be the same or different, each represent hydrogen or linear or branched ($C_1$–$C_6$)alkyl, optionally ($R^2$ and $R^4$) or ($R^1$ and $R^4$) form cyclopropane, $R^5$ represents hydrogen, linear or branched ($C_1$–$C_6$)alkyl or benzyl, the symbol

----- means that the bonds can be single or double, it being understood that the valency of the atoms is respected, wherein alkyl is understood to mean linear or branched alkyl containing 1 to 6 carbon atoms, its tautomers, enantiomers and diastereoisomers, and addition salts thereof with a pharmaceutically-acceptable acid or base.

2. A compound of claim 1, wherein $R^5$ represents hydrogen.

3. A compound of claim 1, wherein $R^1$, $R^2$ and $R^3$ each simultaneously represent hydrogen and Z represents carbon or CH.

4. A compound of claim 1, wherein $R^1$ and $R^2$ each simultaneously represent hydrogen and $R^3$ or $R^4$ represents methyl.

5. A compound of claim 1, wherein ($R^1$ and $R^4$) or ($R^2$ and $R^4$) represent cyclopropane, their tautomers, enantiomers and diastereoisomers, and addition salts thereof with a pharmaceutically acceptable acid or base.

6. A compound of claim 1, wherein the ring system

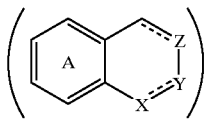

represents 3,4-dihydronaphthalene, 1,2,3,4-tetrahydronaphthalene, indane, indene, or benzofuran.

7. A compound of claim 1, wherein the ring system

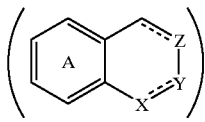

represents 3,4-dihydronaphthalene, 1,2,3,4-tetrahydronaphthalene, indane, indene, or benzofuran, those ring systems being unsubstituted.

8. A compound of claim 1, wherein the ring system

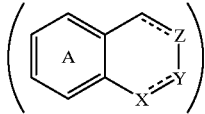

represents 3,4-dihydronaphthalene, 1,2,3,4-tetrahydronaphthalene, indane, indene, or benzofuran, those ring systems being substituted by one or more identical or different substituents selected from halogen and methyl, methoxy and $CF_3$.

9. A compound of claim 1 which is selected from 4-(3,4-dihydro-2-naphthylmethyl)-4,5-dihydro-1H-imidazole, its tautomers, enantiomers and diastereoisomers, and addition salts thereof with a pharmaceutically-acceptable acid or base.

10. A compound of claim 1 which is selected from 4-[(8-chloro-3,4-dihydro-2-naphthyl)methyl]-4,5-dihydro-1H-imidazole, its tautomers, enantiomers and diastereoisomers, and addition salts thereof with a pharmaceutically-acceptable acid or base.

11. A compound of claim 1 which is selected from 4-[(8-methoxy-3,4-dihydro-2-naphthyl)methyl]-4,5-dihydro-1H-imidazole, its tautomers, enantiomers and diastereoisomers, and addition salts thereof with a pharmaceutically-acceptable acid or base.

12. A compound of claim 1 which is 4-(benzo[b]furan-2-ylmethyl)-4,5-dihydro-1H-imidazole, its tautomers, enantiomers and diastereoisomers, and addition salts thereof with a pharmaceutically acceptable acid or base.

13. A compound of claim 1 which is selected from 4-{spiro[cyclopropan-2:2'-(1',2',3',4'-tetrahydronaphth)]-1-yl}-4,5-dihydro-1H-imidazole (isomer 1) and 4-{spiro[cyclopropan-2:2'-(1',2',3',4'-tetrahydronaphth)]-1-yl}-4,5-dihydro-1H-imidazole (isomer 2), its tautomers, enantiomers and diastereoisomers, and addition salts thereof with a pharmaceutically acceptable acid or base.

14. A compound of claim 1 which is selected from 4-[1,2,3,4-tetrahydro-2-naphthylmethyl]-4,5-dihydro-1H-imidazole (isomer 1), 4-[1,2,3,4-tetrahydro-2-naphthylmethyl]-4,5-dihydro-1H-imidazole (isomer 2), 4-[1,2,3,4-tetrahydro-2-naphthylmethyl]-4,5-dihydro-1H-imidazole (isomer 3), and 4-[1,2,3,4-tetrahydro-2-naphthylmethyl]-4,5-dihydro-1H-imidazole (isomer 4), its tautomers, and addition salts thereof with a pharmaceutically-acceptable acid or base.

15. A compound of claim 1 which is selected from 4-(1,3-dihydro-1H-2-indenylmethyl)-4,5-dihydro-1H-imidazole, its tautomers, enantiomers and diastereoisomers, and addition salts thereof with a pharmaceutically-acceptable acid or base.

16. A compound of claim 1 which is selected from 4-[(3,4-dihydro-4,4-dimethyl-2-naphthyl)methyl]-4,5-dihydro-1H-imidazole, its tautomers, enantiomers and diastereoisomers, and addition salts thereof with a pharmaceutically-acceptable acid or base.

17. A compound of claim 1 which is selected from 4-[(7-fluoro-3,4-dihydro-2-naphthyl)methyl]-4,5-dihydro-1H-imidazole, its tautomers, enantiomers and diastereoisomers, and addition salts thereof with a pharmaceutically-acceptable acid or base.

18. A compound of claim 1 which is selected from 4-[(8-chloro-2-naphthyl) methyl]-4,5-dihydro-1H-imidazole, its tautomers, enantiomers and diastereoisomers, and addition salts thereof with a pharmaceutically-acceptable acid or base.

19. Compounds of claim 1 which is selected from 4-{spiro[cyclopropan-2':2"-(5",6"-difluoro-indan)]-1'-yl}-4,5-dihydro-1H-imidazole (diastereoisomer 1), 4-{spiro[cyclopropan-2':2"-(5",6"-difluoro-indan)]-1"-yl}-4,5-dihydro-1H-imidazole (diastereoisomer 2), its tautomers, and addition salts thereof with a pharmaceutically-acceptable acid or base.

20. A compound of claim 1 which is selected from 4-[(5-Fluoro-2,3-dihydro-1H-inden-2-yl)methyl]-4,5-dihydro-1H-imidazole, its tautomers, enantiomers and diastereoisomers, and addition salts thereof with a pharmaceutically-acceptable acid or base.

21. A compound of claim 1 which is selected from 4-[(5,6-Difluoro-2,3-dihydro-1H-inden-2-yl)methyl]-4,5-dihydro-1H-imidazole, its tautomers, enantiomers and diastereoisomers, and addition salts thereof with a pharmaceutically-acceptable acid or base.

22. A method for treating a living body afflicted with a condition of depression, obesity, panic attacks, anxiety, obsessive-compulsive disorders, cognitive disorders, phobias, impulsive disorders associated with the abuse of drugs and withdrawal therefrom, sexual dysfunctions and Parkinson's disease comprising the step of administering to the living body an amount of a compound of claims 1 which is selected from effective for alleviation of said condition.

23. A pharmaceutical composition useful for treating depression, comprising, as active principle, an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 6,127,396  
DATED : Oct. 3, 2000  
INVENTOR(S) : A. Cordi, J-M. Lacoste, M. Millan, A. Newman-Tancredi, A. Gobert Page 1 of 4

It is certified that error appears in the above-identified patent and that said Letters Patent is hereby corrected as shown below:

Column 4, lines (approx.) 33,34,40,48,55: All "$\alpha$" should read: -- a --.

Column 6, lines (approx.) 21,28: All "$\alpha$" should read: -- a --.

Column 7, lines (approx.) 21,22,60: All "$\alpha$" should read: -- a --.

Column 9, lines (approx.) 9,47,67: All "$\alpha$" should read: -- a --.

Column 10, lines (approx.) 18,19,20,45,48,66: All "$\alpha$" should read: -- a --.

Column 11, lines (approx.) 22 and 24: All "$\alpha$" should read: -- a --.

Column 12, lines (approx) 20,23,43: All "$\alpha$" should read: -- a --.

Column 13, lines (approx) 18,19: All "$\alpha$" should read: -- a --.

Column 16, line 66: "formula (X=II)," should read -- formula (XXXIII), --.

Column 22, line 63: At the end of the line, insert -- ] --.

UNITED STATES PATENT AND TRADEMARK OFFICE
CERTIFICATE OF CORRECTION

PATENT NO. : 6,127,396
DATED : Oct. 3, 2000
INVENTOR(S) : A. Cordi, J-M. Lacoste, M. Millan, A. Newman-Tancredi, A. Gobert It is certified that error appears in the above-identified patent and that said Letters Patent is hereby corrected as shown below:

Column 22, line 64: At the beginning of the line, delete "]".

Column 35, line 25: "(1',2',3+,4'-" should read: -- (1',2',3',4'- --.

Column 43, line 1: "LiAlH4" should read: -- $LiAlH_4$ --.

Column 43, line 10: "-1-yl}" should read: -- -1'-yl} --.

Column 43, line 11: "1)" should go on line 10.

Column 43, line 23: "-1-yl}" should read: -- -1'-yl} --.

Column 44, line 64: "-1''-yl}" should read: -- -1'yl} --.

Column 47, line 5: "KCN." should read: -- KCl. --.

UNITED STATES PATENT AND TRADEMARK OFFICE
CERTIFICATE OF CORRECTION

PATENT NO. : 6,127,396
DATED : Oct. 3, 2000
INVENTOR(S) : A. Cordi, J-M. Lacoste, M. Millan, A. Newman-Tancredi, A. Gobert Page 3 of 4

It is certified that error appears in the above-identified patent and that said Letters Patent is hereby corrected as shown below:

Column 47, line 48: Delete the word "from" after "by".

Column 48, line 38: Insert the word -- and -- at the beginning of the line before "optionally".

Column 48, lines 65,66,67: Insert a -- . -- after the word "cyclopropane" and delete the rest of the lines.

Column 49, line 48: After "which is", insert -- selected from --.

Column 50, line 29: "Compounds" at the beginning of the line should read -- A compound --.

Column 50, line 31: Insert -- and -- after "(diastereoisomer 1),".

UNITED STATES PATENT AND TRADEMARK OFFICE
CERTIFICATE OF CORRECTION

PATENT NO. : 6,127,396
DATED : Oct. 3, 2000
INVENTOR(S) : A. Cordi, J-M. Lacoste, M. Millan, A. Newman-Tancredi, A. Gobert It is certified that error appears in the above-identified patent and that said Letters Patent is hereby corrected as shown below:

Column 50, line 32:   "-1''-yl}" should read -- -1'-yl} --.

Column 50, line 50:   "claims 1" should read: -- claim 1 --.

Column 50, line 51:   Delete "selected from".

Signed and Sealed this

Twenty-fourth Day of April, 2001

Attest:

NICHOLAS P. GODICI

*Attesting Officer*   Acting Director of the United States Patent and Trademark Office